United States Patent [19]

Rigoutsos et al.

[11] Patent Number: 5,752,019

[45] Date of Patent: May 12, 1998

[54] SYSTEM AND METHOD FOR CONFIRMATIONALLY-FLEXIBLE MOLECULAR IDENTIFICATION

[75] Inventors: Isidore Rigoutsos, Long Island City; Andrea Califano, New York, both of N.Y.

[73] Assignee: International Business Machines Corporation, Armonk, N.Y.

[21] Appl. No.: 577,759

[22] Filed: Dec. 22, 1995

[51] Int. Cl.$^6$ .................................................. G06F 17/30
[52] U.S. Cl. ........................... 395/603; 395/615; 364/496
[58] Field of Search .................................... 395/615, 603, 395/606; 364/496, 497

[56] References Cited

U.S. PATENT DOCUMENTS

| | | | |
|---|---|---|---|
| 4,811,217 | 3/1989 | Tolizane et al. | 395/603 |
| 4,855,931 | 8/1989 | Saunders | 395/496 |
| 5,418,944 | 5/1995 | DiPace et al. | 395/603 |
| 5,424,963 | 6/1995 | Turner et al. | 364/578 |
| 5,555,366 | 9/1996 | Teig et al. | 395/161 |
| 5,577,239 | 11/1996 | Moore et al. | 395/603 |

OTHER PUBLICATIONS

A. Califano et al, FLASH: Fast Look-up Algorithm for String Homology, Feb. 9, 1995.

J.R. Ullmann, An Algorithm for Subgraph Isomorphism, Journal of the Association for Computing Machinery, vol. 23, No. 1, Jan. 1976, pp. 31–42.

I. Rigoutsos et al, Searching in Parallel for Similar Strings, IEEE Computational Science & Engineering, pp. 60–75 (Summer 1994).

B. Sandak et al, An automated computer vision and robotics-based technique for 3–D flexible biomolecular docking and matching, Oxford University Press, pp. 87–99, vol. 11, No. 1, of CABROS, 1995.

E. Rasmussen et al, Searching of chemical structure data bases with parallel computer hardware, Analytica Chimica Acta, 235 77–86, 1990.

E. Ricketts et al, Comparison of Conformations of Small Molecule Structures from the Protein Data Bank with Those Generated by Concord, Cobra, C ChemDBS–3D, and Converter and Those Extracted from the Cambridge Structural Database, 1993 American Chemical Society, pp. 905–925 vol. 33 No. 6.

D. Fischer et al, Three–Dimensional, sequence order–independent structural comparison of a serine protease against the crystallographic database reveals active site similarities: Potential implications to evolution and to protein folding, Protein Science (1994) 3:769–778.

(List continued on next page.)

*Primary Examiner*—Thomas G. Black
*Assistant Examiner*—Jack M. Choules
*Attorney, Agent, or Firm*—Louis J. Percello

[57] ABSTRACT

A reference storage process populates a data structure so that the data structure contains all of the molecular structures and/or rigid substructures in the database classified according to attributes of tuples. In a preferred embodiment, the tuples are derived from sites (e.g. atomic sites) of the molecular structures and the attributes can be derived from geometric (and other) information related to the tuples. The attributes are used to define indices in the data structure that are associated with invariant vector information (e.g. information about rotatable bond(s) in skewed local coordinate frames created from tuples). These representations are invariant with respect to the rotation and translation of molecular structures and/or the rotation of substructures about attached rotatable bond(s). Accordingly, the invariant vector information is classified in the data structure with the respective tuple attributes in locations determined by the index derived from the respective tuple. A matching process creates one or more tuples, skewed local reference frames, and indices (called test frame tuple indices) for the structure (substructures) of a test molecule using the same technique that was used to populate the data structure. The test frame tuple index accesses the invariant vector information and tallies the frequency of matching in order to determine the identity of molecules/substructures in the database that are structurally similar to the test molecule. This identification can be achieved even in the presence of conformationally flexible molecules in the database.

60 Claims, 11 Drawing Sheets

OTHER PUBLICATIONS

I. Rigoutsos, A Bayesian Approach to Model Matching with Geometric Hashing, Computer Vision and Image Understanding, vol. 62, No. 1,, pp. 11–26 Jul. 1995.

V.J. van Geerestein, et al, 3D Database Searching on the Basis of Ligand Shape Using the SPERM Prototype Method, Tetrahedron Computer Methodology, vol. 3, No. 6C, pp. 595–613, 1992.

K.S. Haraki et al, Looking for Pharmacophores in 3–D Databases: Does Conformational Searching Improve the Yield of Actives? Tetrahedron Computer Methodology, vol. 3, No. 6C, pp. 565–573, 1990.

W. Fisanick et al, Similarity Searching on CAS Registry Substances, J. Chem. Inf. Comput. Sci., 32, pp. 664–674 Summer 1992.

W. Fisanick et al, Similarity Searching on CAS Registry Substances, J. Chem. Inf. Comput. Sci. 1994, 34, pp. 130–140.

Y.C. Martin et al, Searching Databases of Three–Dimensional Structures, Rev. in Computational Chemistry, VCH Publishers, Inc., N.Y. 1990, pp. 213–263.

A.C. Good, New molecular shape descriptors: Application in database screening, Journal of Computer–Aided Molecular Design, 9(1995) 1–12.

T. Hurst, Flexible 3D Searching: The Directed Tweak Technique, J. Chem. Inf. Comput. Sci 1994, 34, 190–196, v34 No. 1.

P. Willett, Ranking and Clustering of Chemical Structure Databases, pp. 191–207, Physical Property Prediction in Organic Chemistry. C. Jochum & M. Hicks (Eds), 1988.

A. R. Leach, et al, Conformational Analysis of Flexible Ligands in Macromolecular Receptor Sites, Journal of Computational Chemistry, vol. 13, No. 6, 730–748 (1992).

M.G. Hicks, et al, Substructure Search Systems, J. Chem. Inf. Comput. Sci. 1990, 30, 191–199.

G. W. Bemis et al, A fast and efficient method for 2D and 3D molecular shape description, Journal of Computer–Aided Molecular Design 6 (1992) 607–628.

P. Willett, A Review of Chemical Structure Retrieval Systems, Journal of Chemometrics, vol. 1, 139–155 (1987).

C. Humblet et al, Section VI: Topics in Drug Design and Discovery, Annual Reports in Medicinal Chemistry–28, pp. 275–284, 1993.

P. Willett, Algorithms for the Calculation of Similarity in Chemical Structure Databases, Concepts and Applications of Molecular Similarity, pp. 43–83, 1990.

P. Willett, Processing of three–dimensional chemical structure information using graph–theoretic techniques, Online Information 90, pp. 115–127, Dec. 1990.

P.A. Bath, et al, Similarity Searching in Files of Three–Dimensional Chemical Structures: Comparison of Fragment–Based Measures of Shape Similarity, J. Chem. Inf. Comput. Sci., 34, 141–147 1994.

J. Greene et al, Chemical Function Queries for 3D Database Search, J. Chem. Inf. Comput. Sci. 1994, 34, 1297–1308.

P. McHale, Access, integration, and interoperability: the MDL approach to inhouse 2D/3D searching, spreadsheets, and QSAR, Proceedings of the 1993.

Chemical Information Conference, Annecy, pp. 46–50, 1993.

R. Nilakantan et al, New Method for Rapid Characterization of Molecular Shapes: Applications in Drug Design, J. Chem. Inf. Comput. Sci. 1993, 33, 79–85.

T. E. Moock et al, Conformational Searching in ISIS/3D Databases, J. Chem. Inf. Comput. Sci. 1994, 34, 184–189.

O.F. Guner et al, Flexible Queries in 3D Searching, Tetrahedron Computer Methodology, vol. 3, No. 6C pp. 557–563, 1990.

B.D. Christie et al, Database Structure and Searching in MACCS–3D, Tetrahedron Computer Methodology, vol. 3, No. 6C, pp. 653–664, 1990.

D.E. Clark, Pharmacophoric Pattern Matching in Files of Three–Dimensional Chemical Structures: Comparison of Conformational–Searching Algorithms for Flexible Searching, J. Chem. Inf. Comput. Sci. 1994, 34, 197–206.

J.E. Dubois et al, DARC Topological Descriptors for Pattern Recognition in Molecular Database Management Systems and Design, J. Chem. Inf. Comput. Sci. 1991, 31, 574–578.

M. F. Lynch et al, Chemical structure retrieval: a review of current research in the Department of Information Studies, University of Sheffield, Chimicaoggi Dec. 1990 vol. 63, pp. 55–63.

J. B. Moon et al, 3D Database Searching and de novo Construction Methods in Molecular Design, Tetrahedron Computer Methodology, vol. 3, No. 6C, pp. 697–711, 1990, p. 697711.

C. A. Pepperrel et al, Implementation and Use of An Atom–Mapping Procedure for Similarity Searching in Databases of 3–D Chemical Structures, Tetrahedron Computer Methodology, vol. 3, No. 6C, pp. 575–593, 1990, p. 575593.

Y.C. Martin, 3D Database Searching in Drug Design, Journal of Medicinal Chemistry, vol. 35, No. 12 pp. 2145–2154, Jun. 1992.

Y. Lamdan et al, Affine Invariant Model–Based Object Recognition, IEEE Transactions on Robotics and Automation, vol.6, No. 5, pp. 577–589 Oct. 1990.

Y. Lamdan et al, On Recognition of 3–D Objects From 2–D Images, Proceedings of the 1988 IEEE International Conference on Robotics and Automation, Apr. 24–29, 1988, pp. 1406–1413.

Y. Lamdan et al, Geometric Hashing: A General and Efficient Model–Based Recognition Scheme, Computer Society of the IEEE, 1988, pp. 237–249.

A. Califano, Multidimensional Indexing for Recognizing Visual Shapes, IEEE Transactions on Pattern Analysis and Machine Intelligence, vol. 16, No. 4, 1994, pp. 373–392.

T. Okada et al, Clusmol: A System for the Conceptual Clustering of Molecules, Tetrahedron Computer Methodology; vol. 2, No. 4, pp. 249–264.

W. Todd Wipke et al, Tree–Structured Maximal Common Subgraph Searching. An Example of Parallel Computation with a Single Sequential Processor Tetrahedron Computer Methodology, vol. 2, No. 3, pp. 177–202, 1989.

R. Nussinov et al, Efficient detectin of three–dimensional structural motifs in biological macromolecules by computer vision techniques, Proc. Natl. Acad. Sci. USA, vol. 88, pp. 10495–10499, Dec. 1991.

R. Norel et al, Molecular surface recognition by a computer vision–based technique, Protein Engineering vol. 7. No. 1 pp. 39–46, 1994.

D. Fischer, Surface Motifs by a Computer Vision Technique: Searches, Detection, and Implications for Protein–Ligand Recognition, Proteins: Structure, Function, and Genetics 16:278–292 (1993).

D. Fischer, An Efficient Automated Computer Vision Based Technique for Detection of Three Dimensional Structural Motifs in Proteins Journal of Biomolecular Structure & Dynamics, ISSN 0739–1102 vol. 9 No. 4 1992.

D. Fischer et al, 3–D Docking of Protein Molecules. Lecture Notes in Computer Science, vol. 684, pp. 20–34, Jun. 1993.

D. Fischer et al, 3–D Substructure Matching in Protein Molecules. Proc. 3rd Symp. Comb. Pattern Matching, 133–147, May 1992.

A. Aho et al, Compilers: Principles, Techniques and Tools. Addison–Wesley, Reading, MA. 1986, pp. 481–485.

M. Garey et al, Computers and Intractability: A guide to the Theory of NP Completeness, W.H. Freeman and Company, N.Y. 1979, pp. 17–35.

SYBYL Release 6.01. Tripos Associates, Inc., 1699 S. Hanley Rd., St. Louis, Mo., pp. 2374–2375, Feb. 1992.

I. Rigoutsos, Massively Parallel Bayesian Object Recognition, Ph.D. Thesis, New York University, N.Y., pp. 1–34, 71–82,96–111 Aug. 1992.

R. Brown et al, J. Chem. Info Comp. Sci 1994, pp. 47–53 "Hyperstructure Model For Chemical Structure Handling Techniques For Substracture Searching".

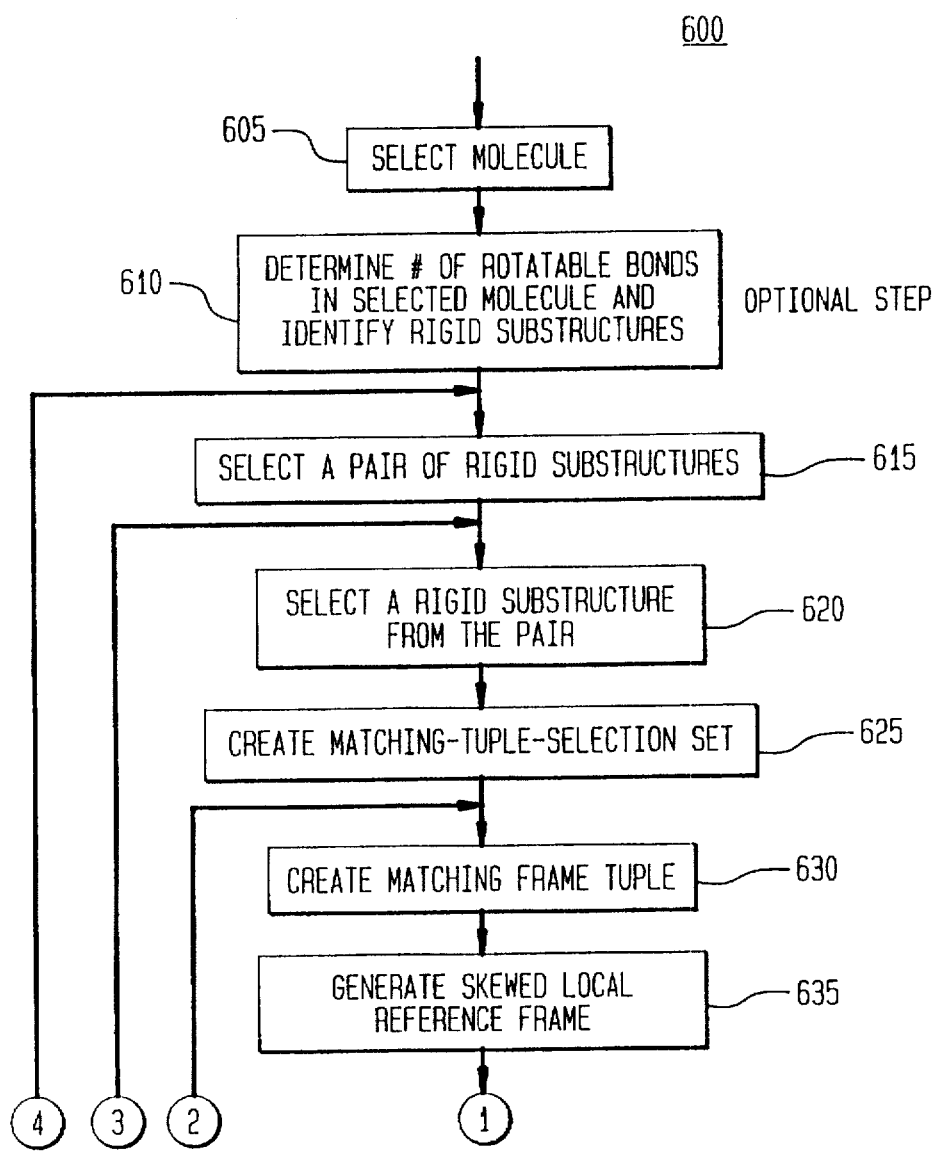

SYSTEM AND METHOD FOR CONFIRMATIONALLY-FLEXIBLE MOLECULAR IDENTIFICATION

1.0 FIELD OF THE INVENTION

This invention relates to the field of computational biology. More specifically the invention relates to a computer system and method for recognizing those molecules in a database of one or more molecules which contain substructures in common with one or more test molecules, even when the molecules in the database contain groups of atoms that are free to rotate around any covalent bonds that may exist in such molecules (torsional flexibility).

2.0 BACKGROUND OF THE INVENTION

As existing information repositories need to be processed more rapidly, and a greater variety of tools become available, the computer plays an increasingly important role in directing and streamlining the drug discovery and design process.

One of the basic ingredients of recent approaches to this line of research endeavor has been the desire to compute, catalog and search molecular properties that are involved in the most fundamental levels of drug interaction.

Specifically, computers can help researchers to quickly eliminate a priori unlikely candidates, thus avoiding long and expensive activity screenings. More important, they can allow researchers to identify new promising compounds based only on the available information on the receptor site, or on other lead compounds.

Being able to perform these tasks quickly and to recover information that can be immediately incorporated into the formulation of the drug search strategy is expected to greatly simplify this complex, multidisciplinary endeavor and to significantly increase the speed at which new and more effective drugs are identified, tested, and brought to the market.

To this date, hundreds of protein structures have been determined via X-ray crystallography and nuclear magnetic resonance (NMR) methods. This data is readily available as a public resource of molecular structure data and allows pharmacologists and biologists to investigate various aspects of protein structures and their complex behaviors. In addition to these public databases, a number of other (public and proprietary) databases of small organic molecules has been assembled through the efforts of numerous pharmaceutical and biotechnology companies, and research organizations.

There are several different scenarios that one is likely to encounter in the process of drug design:

1. A pharmacophore model is proposed from several active molecules; one wishes to find other molecules that either support or refute the pharmacophore hypothesis.
2. A number of untested molecules may exhibit biological activity; one wishes to exploit existing relationships between three-dimensional structure and activity to deduce potentially present biological properties.
3. A certain conformation of a given ligand has been proposed to be biologically active; a three-dimensional search is supposed to identify other molecules which mimic the ligand.
4. The three-dimensional structure of a protein or DNA binding site is available through crystallographic studies. Ligands that fit to the binding site are sought in this case. The search can be augmented by using information about the electrostatic behavior for some of the atomic groups at the site. This technique has been successfully applied by several pharmaceutical companies such as Merck, American Cyanamid, Agouron, etc. to design ligands that bind and inhibit the reverse transcriptase enzyme of HIV.

In each of these cases, the critical information that enables researchers to develop hypotheses, concerning potentially new molecular candidates for synthesis and testing, must be recovered through a search in a potentially very large database of relevant information. Indeed, the underlying common element to several stages of medicinal chemistry investigations is the necessity for searching of chemical information databases. The following will concentrate on the case where the databases to be searched contain structural information pertaining to 3-dimensional atomic compounds.

Typically one is given a compound/molecule C in the form of a set of coordinates of the compound's atomic sites. Also given is a database D, i.e. a collection of sets $D_i=\{\ldots\}$. $D_j=\{\ldots\}$ is a collection of sets of coordinates of the atomic sites for each one of the member molecules. Connecting the various atomic sites in both C and the database members are bonds, some of which may be rotatable and thus allow for torsional flexibility. Torsional flexibility means that the groups of atoms rigidly attached at the two endpoints of a (rotatable) bond can rotate with respect to one another. Each compound/molecule may contain more than one rotatable bond, and thus the compound/molecule can assume any of an infinite number of conformations (three-dimensional configurations) via rotations around these bonds. Occasionally, steric constraints or energy considerations may limit the number of choices, but, the cardinality of the set of possible configurations remains infinite nonetheless. This conformational flexibility of molecular structures opens a broad range of possibilities in the quest for potential ligands, while at the same time rendering the problem exponentially more difficult. In addition to the (internal) torsional flexibility, the molecules are allowed to undergo rigid transformations in three-dimensional space, i.e. the molecule as a whole can rotate and translate. In what follows, the compound/molecule C will interchangeably be referred to as 'test compound' or 'test molecule' or 'query compound' or 'query molecule.'

Given a compound C and a database D containing information about the 3-dimensional structure of a possibly large set of molecules, the following operations need to be defined and carried out:

1. "structure insertion:" the ability to incorporate all available structural knowledge about compound C in the database D;
2. "structure membership:" determination of whether the compound C is already included in the database D;
3. "sub-structure search:" identify and report all the member compounds from D that contain a particular substructure of compound C;
4. "similarity search:" identify and report all the member compounds from D that are similar to compound C. In order to implement such an operation on the database D, a similarity measure d(.,.) needs to be defined and available, and
5. "super-structure search:" identify and report all the member compounds from D that are a substructure of compound C.

First of all, it is easy to see that the predicate of structure membership is subsumed by the substructure search operation. Furthermore, all of the search operations can be reduced to what we will refer to as "substructure similarity."

In what follows, the term substructure similarity is used to refer to a single operation which when given a compound C, a database D and a similarity measure d(...) allows the determination of all the compound-members of D that contain a substructure that is similar to a substructure of C. The extent of the similarity between the molecules in question can be determined by the function d(...). The understanding here is that the implied common substructure may not necessarily be a proper subset of C. The similarity function d(...) will remain unspecified but we assume it to be of a very general nature.

The problem of substructure matching can be shown to be NP-complete by noting that it includes the problem of subgraph isomorphism as a special case. The real-world implication of this statement is that the time complexity for finding all optimum solutions is an exponential function of the length of the input, and thus no efficient (i.e. polynomial time complexity) algorithm exists for finding optimum solutions. The computational complexity of the problem is further compounded by allowing torsional flexibility around the molecule's covalent bonds.

Before concluding this section a final distinction should be noted. This is the distinction between 'identification' and 'recognition' of those molecules from the database D of molecules which are similar to the given test compound/ molecule C. Identification restricts itself to reporting only the identities of the molecules from database D that match the test compound/molecule C. On the other hand, recognition entails not only the reporting of the identities of the matching molecules but also the determination and reporting of the necessary transformations that will bring each of the identified matching molecules to "best registration" with the test compound/molecule. ("Best Registration" positions the atomic sites of the test molecule and matching database molecules in such a way that the number of locations in three-dimensional space that would be occupied at the same time by atoms of the test molecule and atoms of each matching database molecule is the maximum possible). These "necessary" transformations include rotations and translations of the molecules under consideration as a whole but also rotations of structures within the molecules around the molecules' torsionally flexible bonds.

Recognition is arguably a much more difficult problem than identification; this is particularly evident in the case of very large databases D, with molecules that are torsionally flexible. This happens because the number of possible transformations increases exponentially with the number of rotatable bonds that allow for the exhibited torsional flexibility: the computational considerations for finding and reporting the correct transformation, in general, increase with the number of transformations.

3.0 PROBLEMS WITH THE PRIOR ART

The inherent computational complexity of the substructure similarity task has typically plagued all of the previously suggested approaches for tackling this problem. Even when one restricts the problem to the case of rigid molecules with no rotatable bonds, the problem remains computationally very demanding because of its three-dimensional nature.

In order to appreciate the complexity of the task, a one-dimensional analog from everyday life is presented. Given a shelf full of books and a sentence such as "forming 3D queries that can accommodate certain flexibility in the target structures,"

a search task is defined as the need to find all occurrences of similar phrases in the set of available books. Similar, in the most general case, means that a phrase such as "we form a 3D search query so that it accommodates desired flexibility"

should be reported as being a valid match. In other words, operations such as replacement, insertion, and deletion of the most fundamental information elements (in this case the letters) are legitimate and thus allowed. (In the case of molecules the most fundamental information elements are the atoms of a molecule).

A straightforward approach to solving this task entails the scanning of the contents of all the books of the shelf in an exhaustive, linear fashion, i.e. left-to-right, top-to-bottom, in order to locate all similar (in this case one-dimensional) structures. Clearly, such a mode of operation will require increasingly more time as the number of books on the shelf (i.e. the size of the database) increases.

Of course, a number of heuristics can facilitate finding the answer. For example, certain operations may not be allowed, or the search could be restricted to a smaller, well-specified set; this immediately restricts the number of possible variants for a given phrase and makes precomputation and storing of alternative phrases plausible. When searching, the test phrase is compared against the set of all allowed, precomputed variants.

Alternatively, "keys" can be precomputed using a subset of words within a window of prespecified width, and stored. When presented with a query the system computes the set of keys for the query and uses them to search and find the set of keys which have been computed for all the phrases in all the books. In other words, instead of comparing the phrases directly with one another, their "representatives" are compared instead, again in a linear fashion.

A situation analogous to the above similar-phrase search task exists in the case of searching for similar structures in databases of three-dimensional molecular information. The following presentation of representative techniques intends to help identify the commonalities and differences of previously suggested approaches.

The various techniques that have been proposed over the years for searching three-dimensional molecular databases basically differ in their definition and their use of the similarity measure d(...) which was introduced above. Given a test compound C and a database D, the similarity measure d(...) evaluates the extent in which C and a given member of D are similar. The values produced by comparing C to each one of the member molecules of D will produce a "score" that can subsequently be used to rank candidate answers in order of decreasing quality.

For example, in the "atom-mapping" method the Tanimoto coefficient is computed using the result of pairwise comparisons of the rows from the distance matrices of two molecules. This coefficient is used as an entry to an intermolecular similarity matrix. This matrix is used in conjunction with a greedy algorithm to establish the degree of similarity between the two molecules. The calculation is repeated for all the combinations between a query molecule C and each of the molecules in the database D. As is the case with greedy algorithms, no guarantees exist that the algorithm will find all of the correct solutions. The approach is computationally very demanding and does not scale well with database size.

In the "clique-detection" method a number of different orientations is generated for each of the molecules in the database prior to comparing it to the query molecule C. Each of the orientations is then overlaid on C and scored based on the presence or not of database atoms in the vicinity of an atom of C. All of the orientations that lead to score less than the maximum are discarded. The search then continues with the next molecule of the database. At any point during the search, the last n best scores are retained. This technique is at the core of the Mosaic molecular modeling system.

In other prior art techniques the molecular structures are represented as connection tables, and thus viewed as graphs. The vertices of each such graph correspond to the molecule's atomic sites. If a bond exists between two given atomic sites, then the corresponding graph will have an edge connecting the relevant nodes. If each molecule of the database D is represented by a graph, one can carry out a search for similar substructures by using subgraph isomorphism algorithms. As we have already mentioned above, the problem of subgraph isomorphism is NP-complete and thus no efficient algorithms exist. Recent work compared a number of different subgraph isomorphism algorithms and presented evidence for the usefulness of a backtracking search algorithm enhanced with the "refinement procedure" heuristic. Graph-theoretic results are also used to develop similarity functions for comparing molecular fragments (substructures).

A variation of the above scheme begins by clustering all of the molecules in the database D into several clusters. In this case, the similarity measure $d(.,.)$ is first used to calculate intermolecular similarities for all the pairs that can be formed by molecules in D. Subsequently, a clustering step is used to group the various molecules into clusters based on the values produced by the pairwise comparisons. When presented with a query molecule C, this approach classifies C by identifying the cluster in which C belongs. The molecules of database D which best match the query molecule C are drawn from this cluster as well as the neighboring cluster (or clusters).

So far, the assumption has been that the molecules under consideration are rigid three-dimensional structures. But most of the time, this is not the case. Usually, molecules have several internal rotatable bonds, and are thus able to assume a continuum of conformations, i.e., three dimensional configurations. Occasionally, steric constraints or energy considerations may limit the number of choices.

Treating the molecules of a database as rigid facilitates the search in 3D databases at the expense of discarding large numbers of valid candidates: although the stored conformation of a molecule may not exhibit the pharmacophoric pattern/model under consideration, a different conformation of the same molecule may be biologically active. Thus, conformational flexibility of molecular structures opens a broad range of possibilities in the quest for potential ligands. But, at the same time, it imposes a serious burden on the search component of the conventional approaches.

Given a database D of molecules, one straightforward approach that allows any search algorithm to carry out conformationally flexible searches in D entails the storing of all the conformations of each of the molecules in D. In practice, given that there is a continuum of possible conformations, a large number of representative conformations is stored instead. The implications of such an approach are evident: the resulting databases will have overwhelming sizes and very long search times will be necessary. An alternative approach to storing all possible conformations involves storing each molecule in only one (or a handful) of conformations. For example, the Concord-3D system uses a set of rules to generate a single conformation using the molecule's connection tables. These approaches in essence belong to a class of methods that puts the flexibility in the database.

In an analogous manner, a variant of this method applies a set of rules (determined by performing a systematic conformational analysis on chains of various combinations of six backbone atoms) to examine the conformational space and retain only certain torsion angles for each rotatable bond: a set of "low-energy" conformations together with their corresponding "screens" is produced. These screens are subsequently used during the actual search of the database. In a related approach, a large number of conformations of a database molecule is generated during the search and compared with the pharmacophoric pattern. This is a computationally heavy approach, and any attempts (through the use of heuristics) to reduce this burden have a direct impact on the quality of the produced results: otherwise valid matches will now be missed. Both of these methods are representative of a class of techniques that put the conformational flexibility into the search.

There is also a third approach, where the flexibility is put in the query itself. The query in this case combines both rigid and flexible components and is iteratively refined by searching a database of compounds with "known" activity until the desired selectivity is obtained. Once the final query is available, it is used to search a database of compounds with "unknown" activities to identify potential leads.

The more successful search techniques attack the problem of conformational flexibility in a computationally demanding way; the conclusion of previous work was that flexible three-dimensional searching using the approach developed by Clark et. al. incurs a minimum of a 100-fold slowdown over the rigid matching case. This slowdown appears to be typical and independent of the actual technique that is employed.

In a comparison study by Haraki et. al. it was shown that augmenting a database with multiple conformations of a given molecule enhances in general a search algorithm's performance. But the same study also established that the resulting effectiveness largely depends on the method which is used to generate the various conformations to be added in the database.

As an alternative to the multiple inclusion of a molecule in the database, a certain type of minimization is carried out in "discrepancy space." This approach is much faster but it requires certain relations between the number of structural constraints and the number of existing rotatable bonds; furthermore, it inherits all of the problems of non-linear optimization approaches.

Yet another type of technique tries, essentially, to perform rigid docking only on the rigid subparts of the molecule and then check the compatibility of the various docked parts in a post-processing phase. This technique is in general computationally very demanding.

A number of shortcuts in the form of search heuristics have been introduced to alleviate some of the computational burden, but not without adverse impact on the quality of the produced results. To counterbalance this statement, these heuristics are of a more general applicability and can also be used in the case where conformational flexibility is not one of the parameters of the problem.

In particular, some prior art gives a very thorough presentation and carries out a comparative study of a number of descriptors for the purposes of database screening. The descriptors cover a large range of properties of the molecules in the database: physical, chemical, geometric as well as several combinations thereof. The discrimination ability of some of the proposed descriptors is encouraging but the results have been obtained using a small database with only a few thousand compounds.

Related work introduces a two-stage method that in essence characterizes shape without the need for examining a multitude of docking orientations. In the first stage, a 2048-bit number is generated for each of the molecules in the database by setting appropriate bits in a bit-vector. The bits to set are selected based on a 32-bit encoding of each triangle formed by three atomic sites in the molecule. Clearly, the number captures geometric characteristics which are particular to each molecule; however, due to the way it is generated, the representation is not unique. During the second stage, a similar 2048-bit is generated for the test molecule and is compared with each of the stored signatures. For those molecules whose signatures exceed threshold, triplets of atomic sites are formed again and compared against the triplets in the test molecule for intersection. Although the method does not recover the relative orientation between a candidate and the test molecule it appears to be adequate as a screening step.

In all of the described prior art, the techniques either do not scale well with the size of the database (due to the need for a serial scan and processing of all the entries), or do not fully exploit the constraints imposed by the rotatable bonds in order to limit the extent of the search.

Unlike the techniques that require a linear scan of the database D, hashing techniques are based on the identification of certain invariant descriptors (indices) that can be used to store-in a look-up table a partial representation of, say, a molecule. Compatible molecules can be retrieved by computing the indices from a test input, retrieving the partial representation from the look-up table, and integrating the evidence directly, thereby eliminating the need to scan the entire database for one or more matches. For molecules, indices can be formed by using tuples of atoms (e.g., triplets) with atom properties or tuples of small surface patches associated with their normals and the chemical properties at the surface (two independent patches are sufficient in this case.

In previous work it has been argued that using indices of a high dimensional nature (with a large number of distinct values) is crucial for the correct behavior of these techniques when the size of the database becomes large. Two main issues contribute to this very general result. First, bins in a look-up table with a larger set of bins will be, on the average, less crowded. And second, coarser quantization can be used along each of the index dimensions thus increasing the probability of recovering the same index during retrieval of similar entities.

Unlike the scan-based techniques though, the class of hashing algorithms has increased storage requirements. In particular, the various instantiations of the algorithm derive their speed by precomputing results and storing them in appropriately constructed lookup-tables. This precomputation can be performed off-line, is done only once, and the results are stored on disk and used when needed. The hashing approach in essence trades space for computation; in the face of decreasing slow-storage costs the trade-off is becoming increasingly justifiable and reasonable.

4.0 OBJECTS OF THE INVENTION

An object of this invention is an improved computer system and method for identifying those molecules from a database D containing one or more molecules which contain substructures in common with substructures from one or more test molecules C, even when the molecules in the database contain groups of atoms which are free to rotate around any covalent bonds that may be present in the molecule (torsional flexibility).

5.0 SUMMARY OF THE INVENTION

This system and method identifies molecules and/or molecular substructures in a database that are similar or identical to one or more test molecules and/or substructures and/or parts of substructures of these test molecules.

The invention uses a reference storage process to populate a data structure so that the data structure contains all of the molecular structures and/or substructures in the data base classified according to attributes of tuples. In a preferred embodiment, the tuples are derived from sites (e.g. atomic sites) of the molecular structures (substructures) chosen to create the tuples and the attributes are geometric (and other) information related to the chosen tuples. The attributes are used to define indices in a data structure that are associated with invariant vector information (called vector information) pertaining to the molecules of the database D. For example, the invariant vectors can represent rotatable bonds in reference molecules in the database D. These invariant vectors (e.g. rotatable bonds) are represented in skewed local coordinate frames created from tuples derived from rigid molecular substructures to which the vector(s) is (are) attached. These representations are invariant with respect to the rotation and translation of molecular structures and/or the rotation of substructures about the attached rotatable bond. Accordingly, invariant vector information pertaining to molecules in the database can be classified with respect to the tuple attributes by storing the invariant vector information in locations (vector fields) of the data structure associated with the index derived from the respective tuple. Once the data structure is populated, a matching process creates one or more tuples, skewed local reference frames, and indices (called test frame tuple indices) for the structure (substructures) of a test molecule using the same technique that was used to populate the data structure. The test frame tuple index is used to access the invariant vector information that is in the vector field of the data structure index which matches the test frame index. A tally is kept of the frequency of matching vector information (indices) of molecular structures (substructures and/or parts) in the database to the test frame tuple indices generated for the test molecule to determine which molecular structures (substructures and/or parts) identically or similarly match those in the database.

6.0 BRIEF DESCRIPTION OF THE DRAWINGS

The foregoing and other objects, aspects, and advantages of the invention will be better understood from the following detailed description of preferred embodiments of the invention with reference to the drawings described as follows:

FIG. 1 is a block diagram of a computer system embodying the present invention.

FIG. 2A is a diagram of a molecular structure showing rigid substructures of atom groups in the molecule, the rotational nature of a typical rotational bond between rigid substructures, a global coordinate frame, a skewed local coordinate frame, a "frame-tuple" defining the skewed local coordinate frame, and a representation of an invariant vector connecting two points on one or more rigid substructures, and a first conformation of the molecular structure.

Figure 4:
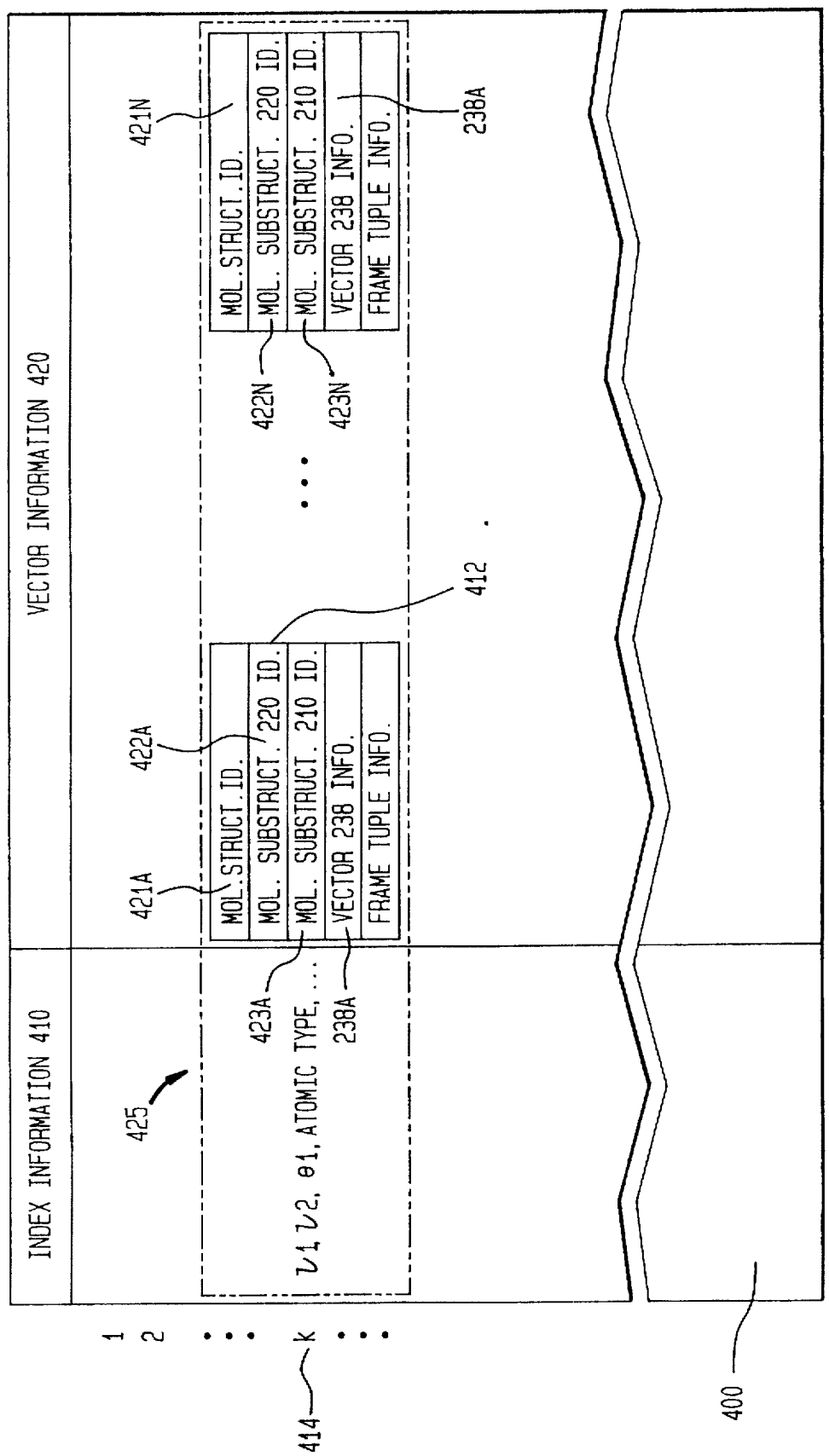
FIG. 4 is a block diagram of a data structure that associates an index corresponding to a tuple with vector information that corresponds to the representation of an invariant vector in each of the skewed local coordinate frames of the tuple generating the index.
Figure 5A:
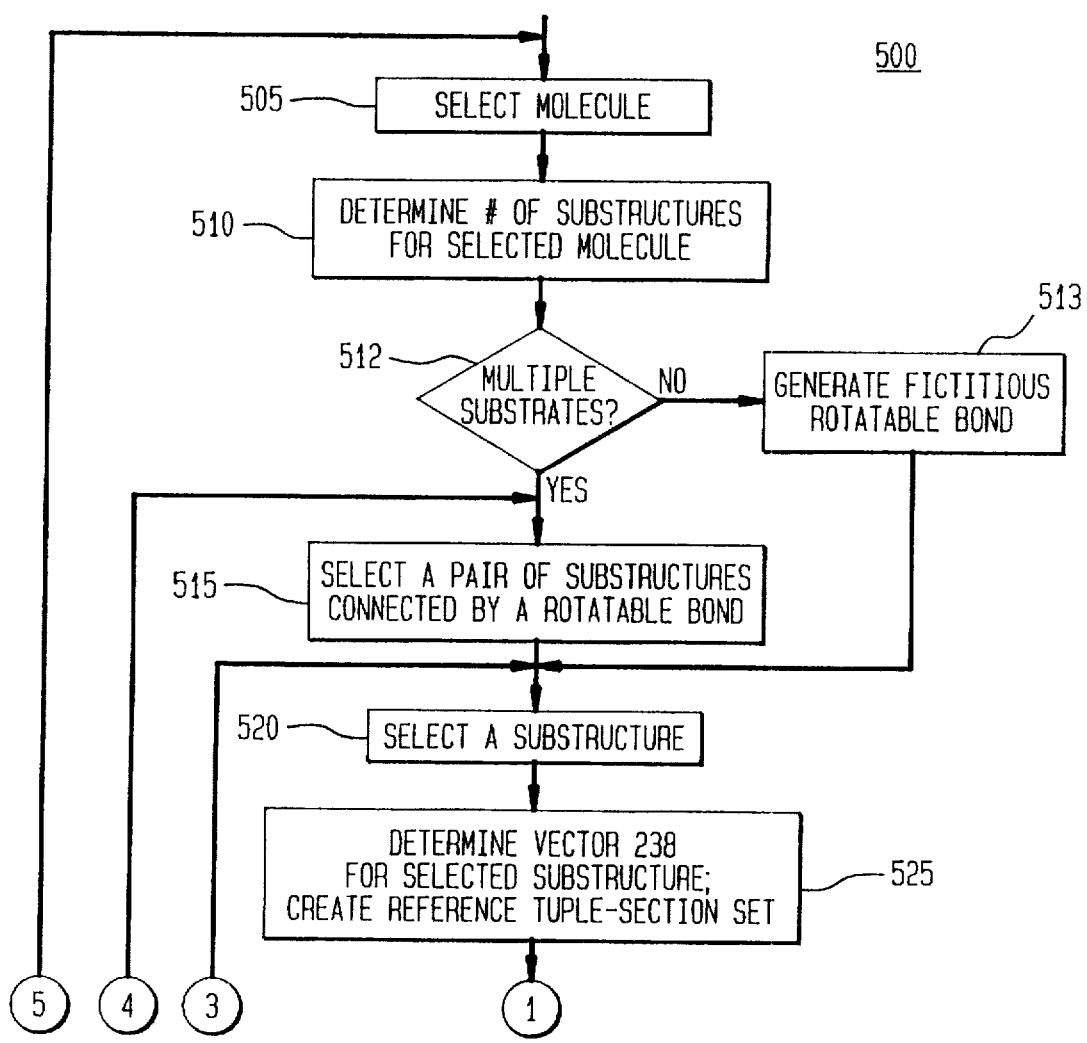
Figure 5B:
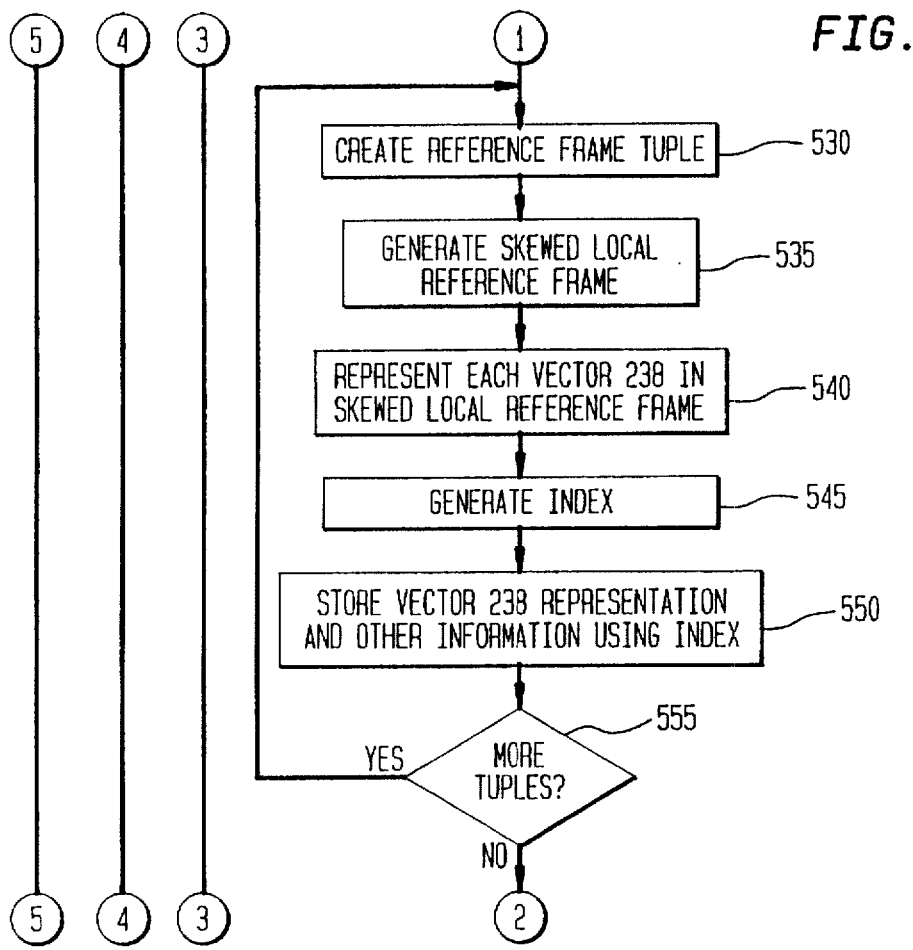
Figure 5C:
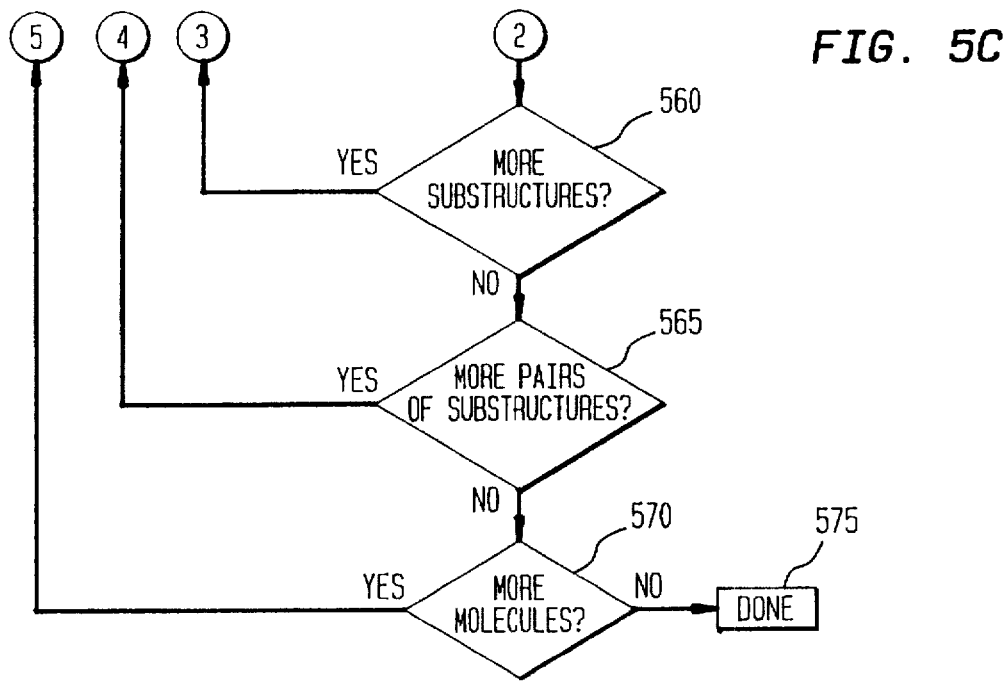

FIG. 5, comprising FIGS. 5A, 5B and 5C, is a flow chart showing the steps of populating the data structure of FIG. 4 to contain structural information and other information about one or more reference molecules.

Figure 6B:
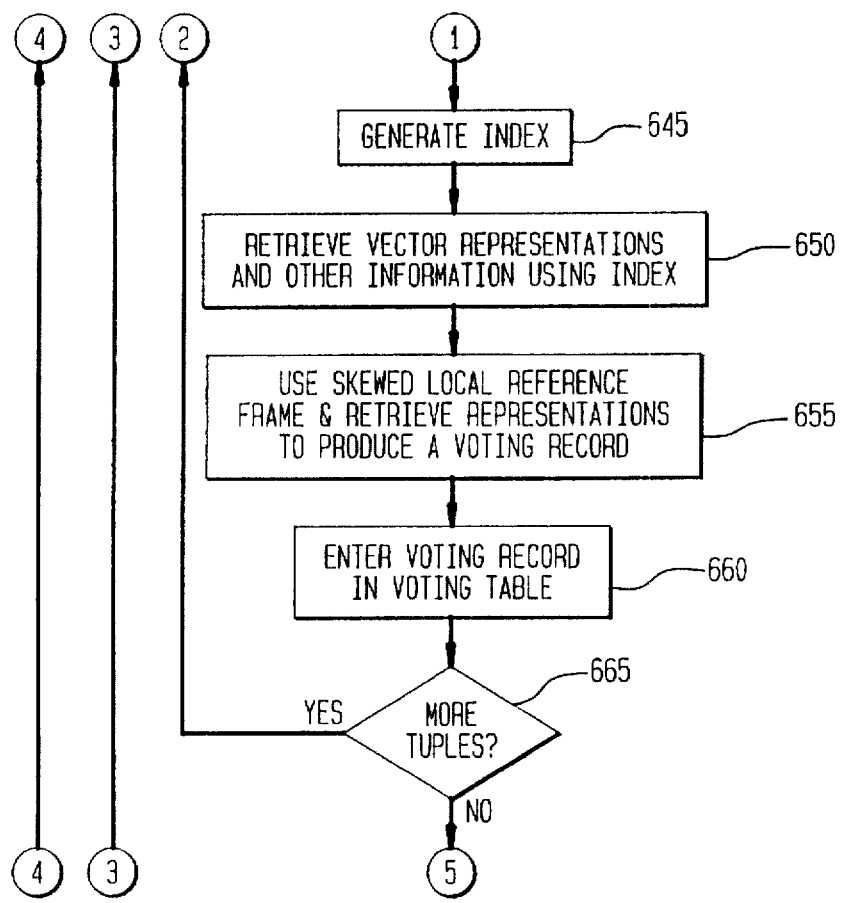
Figure 6C:
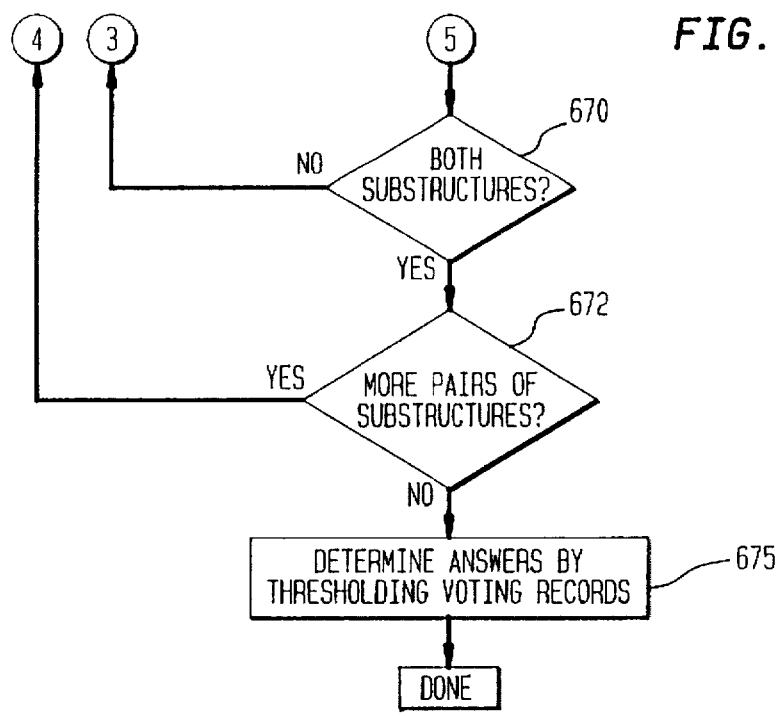

FIG. 6, comprising FIGS. 6A, 6B and 6C, is a flow chart of a preferred method showing the steps of determining which reference molecules in the library (database D) containing one or more molecules are similar to (=match) a test molecule for a selected set of one or more molecular characteristics.

Figure 7:
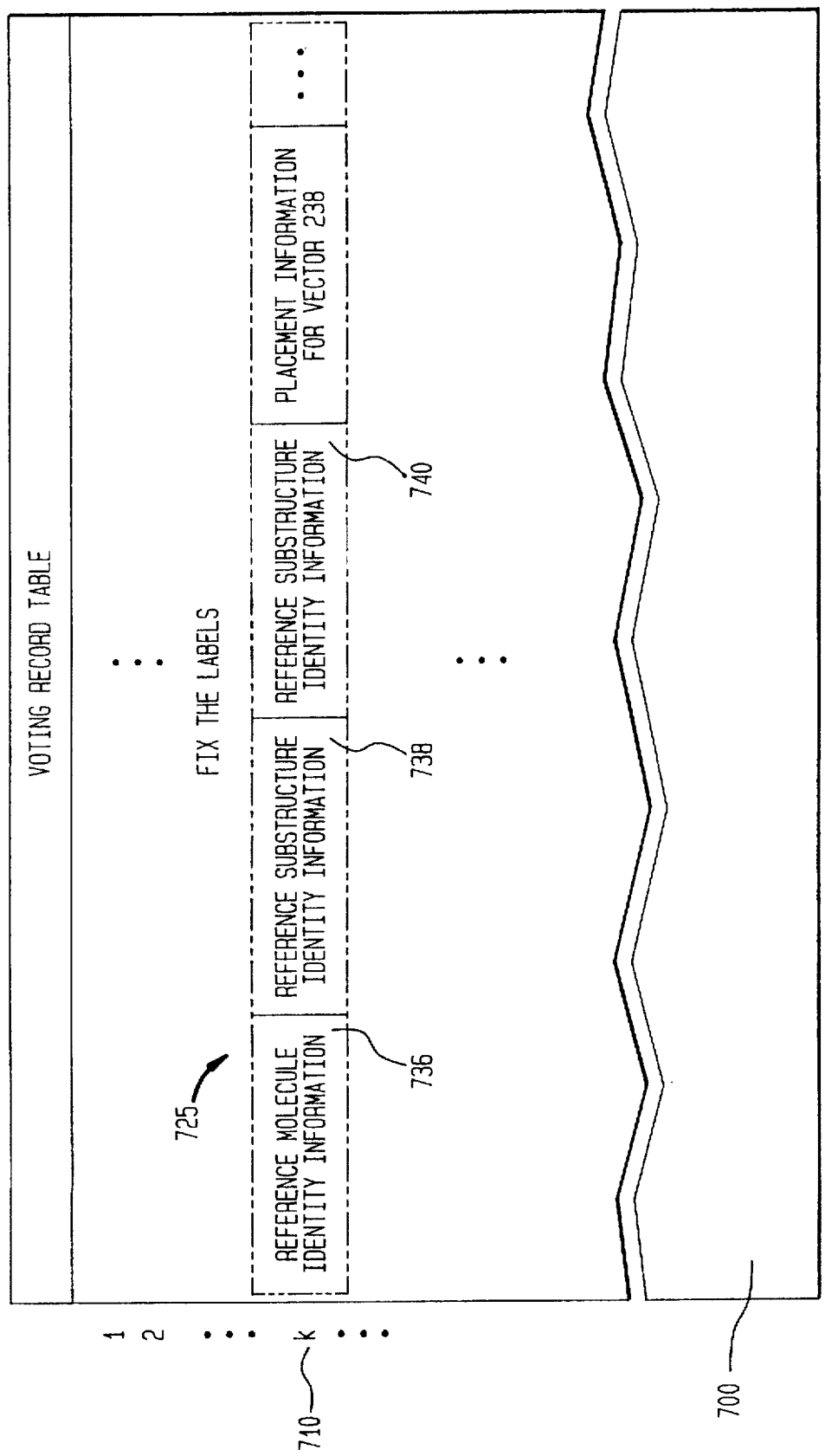

FIG. 7 is a block diagram of a voting table used to determine the relative frequency (multiplicity values) of the identities of those molecules and/or molecular substructures in the database D which match the test molecule for a given set of molecular characteristics.

7.0 DETAILED DESCRIPTION OF THE INVENTION

Figure 1:
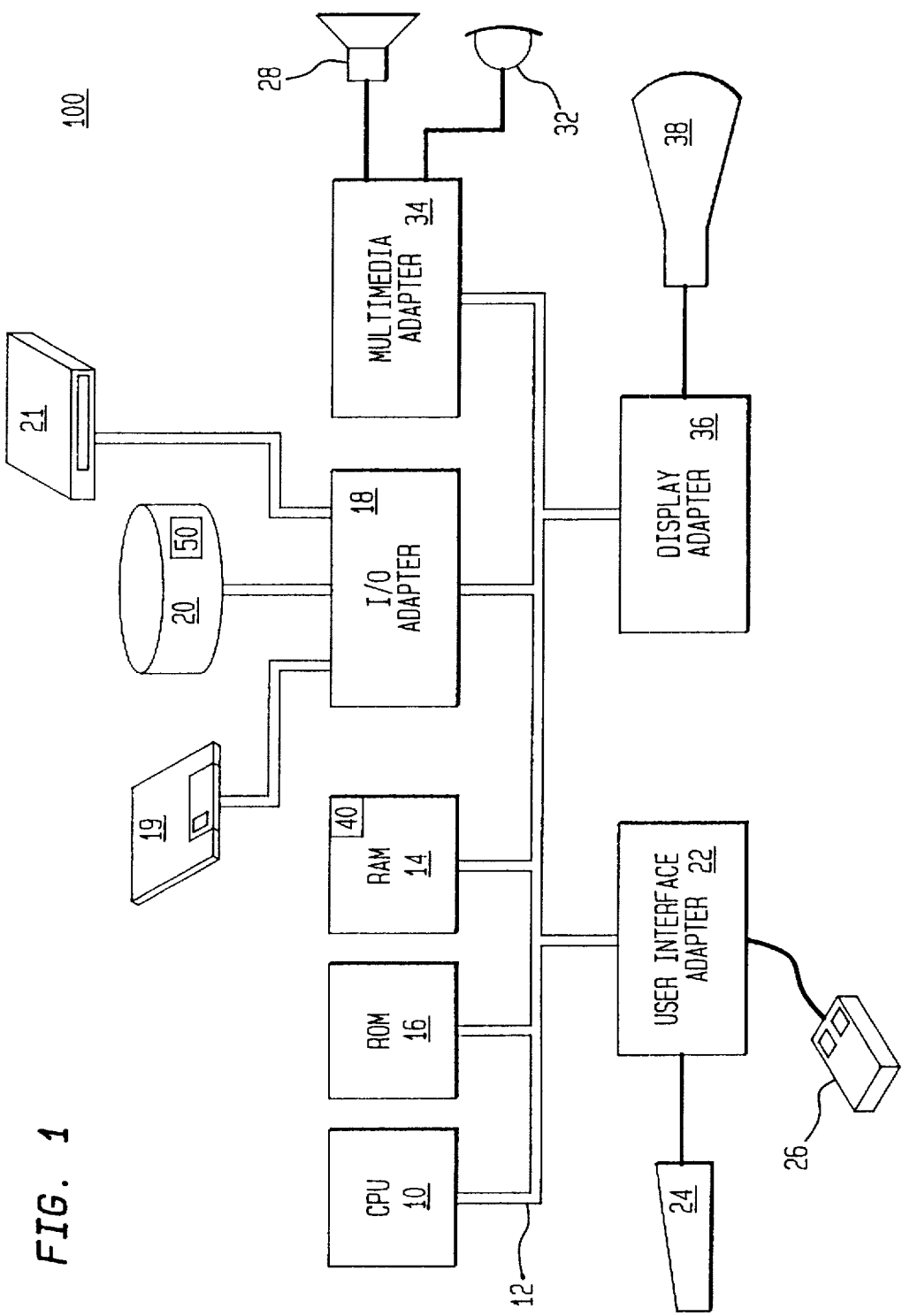

Referring now to the drawings, and more particularly to FIG. 1, there is shown the block diagram representation of a general computer hardware environment 100. This computer 100 may be one of International Business Machines Corporation (IBM) Personal System/2 (PS/2) family of Personal Computers, a RISC System/6000, or Power Parallel System (SP/x). The system 100 includes one or more central processing units (CPU) 10, which may conform to Intel's x86 architecture or may be a reduced instruction set microprocessor. The CPU 10 is attached to a system bus 12 to which are attached a read/write and/or random access memory (RAM) 14 that can include one or more cache memories, a read only memory (ROM) 16, an input/output adapter 18, and a user interface adapter 22. The RAM 14 provides temporary storage for one or more application program 40 containing code and/or data while the ROM 16 typically includes the basic input/output system (BIOS) code. The I/O adapter 18 is connected to one or more Direct Access Storage Devices (DASDs), here represented as a floppy drive 19, a hard disk drive 20, and a CD-ROM 21. The hard disk drive 20 typically stores the computer's operating system (OS), such as IBM's OS/2 operating system, and various application programs, data, and/or databases 50, each of which can be selectively loaded into RAM 14 via the system bus 12. The user interface adapter 22 has attached to it a keyboard 24, a mouse 26, and/or other user interface devices (not shown).

The system 100 also can include a display 38, here represented as a cathode ray tube (CRT) display but which may be a liquid crystal display (LCD) or other suitable display and/or graphic user interface (GUI). The display 38 is connected to the system bus 12 via a display adapter 36. A multimedia adapter 34, such as an Intel Corporation's ActionMedia II Display Adapter, can also be connected to the bus 12 and to a microphone 32 and a speaker 28. The multimedia adapter 34 is supported by suitable software, such as a Multimedia Presentation Manager/2. These systems 100 and equivalents of these systems are well known to those skilled in the art.

Personal System/2, PS/2, OS/2, RISC System/6000, Power Parallel System, SP/x, and IBM are trademarks of the International Business Machines Corporation.

Some of the application programs 40 will be described as process methods below. Molecular databases 50, also described below, are typically stored on the storage devices, e.g. the hard disk drive 20.

Figure 2A:
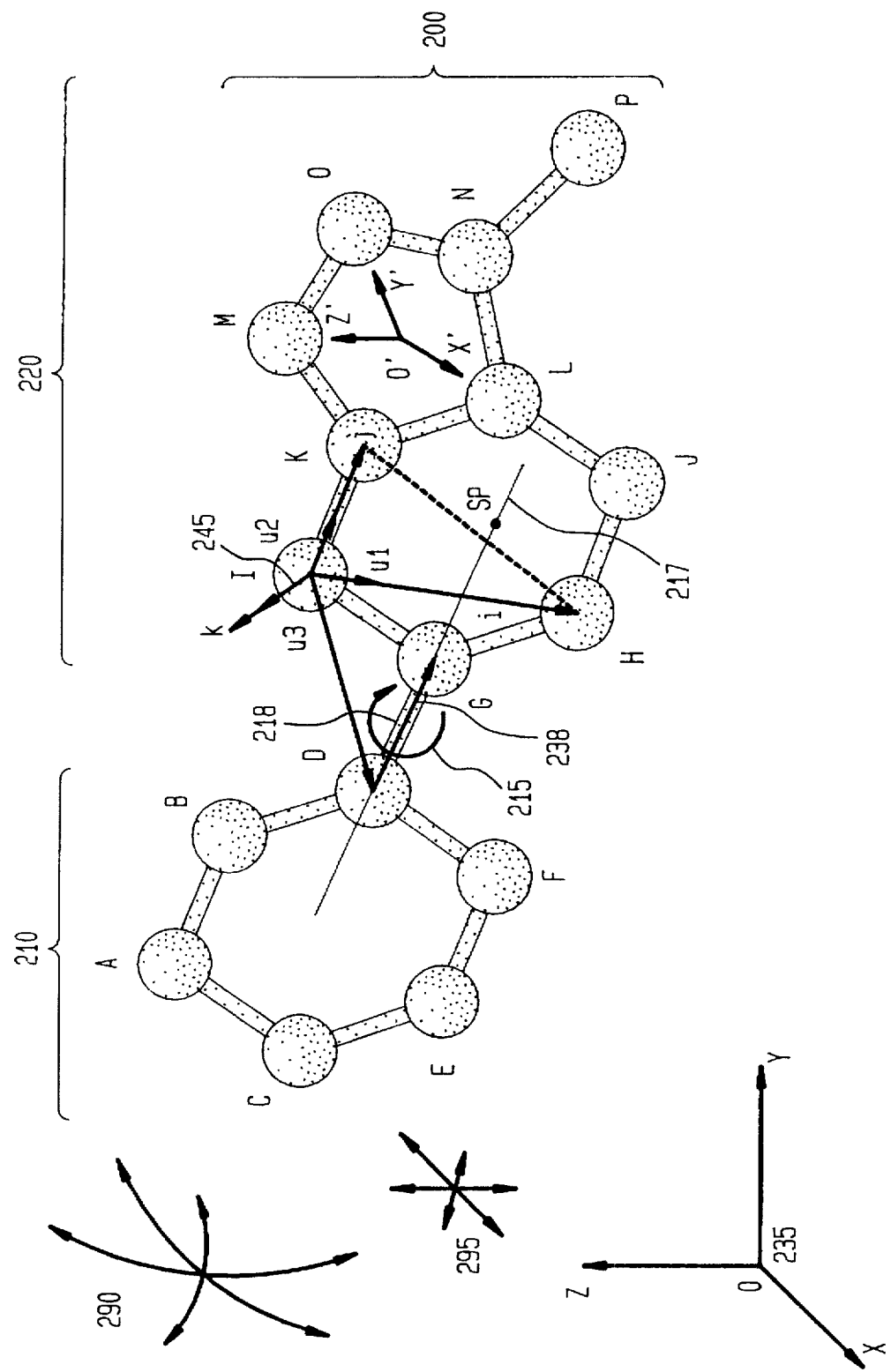
FIG. 2B is a diagram showing a second molecular conformation of the molecular structure, the global coordinate frame, the skewed local coordinate frame, and the invariant vector of FIG. 2A.

FIG. 2A is a diagram of a molecular structure 200 showing rigid substructures (210,220) of atom groups in the molecule 200, the rotational nature 215 of a typical rotatable bond 218 between rigid substructures (210,220), a global coordinate frame 235, a skewed local coordinate frame 245, a "frame-tuple" defining the skewed local coordinate frame 245, and a representation of an invariant vector 238 connecting two points (D, G) on one or more rigid substructures (210,220), and a first conformation 200 of the molecular structure.

Defined and clarified below are some of the terms that will be used extensively in the text. A molecular structure (200, 250) is a set of atoms (e.g. A–P) connected with one another through chemical bonds, typically MO. (Bonds are designated by pairs of letters corresponding to the two atoms connected by the bond). In general, the molecular structure 200 is typically defined through a set of coordinates for the sites occupied by the various atoms. For example, coordinates (x,y,z) define the position of atom 0 in the global (laboratory) coordinate frame 235. The global coordinate frame 235 is assumed fixed and constant for the purposes of the analysis below.

Further, a list of the chemical bonds connecting the sites with one another, e.g. MO, also defines the molecular structure 200. The various sites (A–P) of the molecular structure 200 and/or the respective atoms occupying these locations in the global coordinate frame 235 are typically given labels (for example: a number) that distinguish them from one another. For our purposes, we will use interchangeably a letter (e.g. A–P) and/or a number to label the atom and/or the site where the atom is located in the global coordinate frame 235.

Finally, in addition to the list of the site coordinates and the list of chemical bonds, a list of the atomic types (e.g. N, C, O, H, etc.) for each of the atoms occupying the various sites of the molecular structure is provided.

Note that occasionally, a molecular structure is specified using the list of chemical bonds and the list of atomic types for each of the atoms participating in the structure. A molecular structure that has been defined in such a way is by no means undetermined: indeed, the coordinates of the atomic sites can be recovered from the given information using a variety of standard methods.

A bond, MO, represents a chemical connection between two atoms (M, 0) in the molecular structure 200. Bonds are typically defined in terms of the labels associated with the two atomic sites that the bond connects.

Some of the bonds in a given molecule may be rotatable and thus allow for torsional flexibility 215: the rigid substructures (210,220) are attached at the two endpoints of a rotatable bond and therefore can rotate 215 with respect to one another.

Within each of the two rigid substructures (210,220) on either side of a rotatable bond 218, atoms are connected to one another with bonds which do not allow such torsional flexibility (non-rotatable bonds—AC,MO).[1] Therefore, rigid substructures (210,220) are structures of one or more atoms connected to one another through non-rotatable bonds. Groups consisting of one atom, P, bonded through bonds like NP to a set of atoms like G,H,I,J,K,L,M,N, and O are not considered separate rigid substructures despite the fact that the bond NP may be rotatable. This is because any rotation of atom P around the bond NP does not change the location of P in the global coordinate frame 235. Furthermore, any rotation of atom P around the bond NP does not change the location of P with respect to the set of atoms G,H,I,J,K,L,M,N, and O. Note also that rigid molecules, i.e. those molecules that contain no rotatable bonds, can be defined as molecules of one rigid substructure; in such a case, the entire molecule is the substructure (210,220).

[1]. This is not true in the general case: there exist molecular substructures which exhibit hinge-like flexibility, but a treatment of these substructures escapes the scope of this analysis.

Note also that defining the coordinates (x, y, z) of three or more atoms (sites) (e.g. G–P) of a given rigid substructure 220 in the global coordinate frame 235 suffices to define a global position OO' and a global orientation (O'x', O'y', O'z') for the rigid substructure 220 in the global coordinate frame 235. Note additionally that the set of three or more atoms (sites) that define the global position and orientation for the rigid substructure 220 can include the atom (site) D because the rotation 215 around rotatable bond 218 of the rigid substructure 210 with respect to the rigid substructure 220 does not change the position of atom (site) D with respect to the rigid substructure 220. Likewise, in defining a global position and orientation for the rigid substructure 210 the set of three or more atoms (sites) could include atom (site) G in addition to the atoms (sites) A–F.

Consequently, the vector 238 which is defined below, has a fixed position and orientation with respect to either rigid substructure 210 or 220 that the rotatable bond 218 connects. This happens because the position and orientation of the rotatable bond 218 with respect to either rigid substructure does not change despite the rotation in the global coordinate frame 235 of either of the substructures about the rotatable bond 218.

In the following, the term rigid substructure (210,220) may be used interchangeably with the term rigid group (210,220).

As will be discussed below, the vector 238 which as already mentioned has a fixed position and orientation with respect to either rigid substructure 210 or 220 need not be defined in terms of the rotatable bond 218 emanating from the rigid substructure 210,220. Indeed, for a given rigid substructure, vector 238 can be any vector that can be defined to be rigidly placed with respect to the rigid substructure.

For the moment, vector 238 is defined with the help of rotatable bond 218: for example, the magnitude and direction of the vector 238 coincide with those of the bond 218. The convention for the direction is assumed to be from the lower-(higher-) numbered substructure (210,220) to the higher-(lower-) numbered substructure (210,220) consistently for all of one or more molecular structures 200 analyzed. An alternative convention for the direction is based on the labels of the atoms (sites) at the endpoints of a rotatable bond: the direction is assumed to be from the lower-(higher-) numbered atom (site) to the higher-(lower-) numbered atom (site) consistently for all of one or more molecular structures 200 analyzed.

A given molecular structure 200 may contain more than one rotatable bond 218, and can thus assume any of a possibly infinite number of conformations (200,250) via rotations around these bonds 218. Molecular structures 200 with one or more rotatable bonds 218 are referred to as "conformationally flexible" molecular structures or "conformationally flexible" molecules.

Notice that molecular structure 250 is another conformation of the molecular structure 200 (and vice versa) because it is the same molecular structure with its rigid substructures (210,220) rotated 215 about rotatable bond 218 with respect to one another.

Alternatively, a given molecular structure 200 may contain no rotatable bonds 218, and it is then referred to as a "rigid" molecular structure or a "rigid" molecule.

In addition to the conformational flexibility of a molecular structure (200,250) through rotations around its rotatable bonds 218, the entire molecular structure (200,250) can also rotate 290 with three degrees of freedom and translate 295 with three degrees freedom in the global coordinate frame 235.

In addition to the global coordinate frame 235, one can also form "local" coordinate frames 245 by appropriately selecting a small set of atomic sites (e.g. I, K, H) in the molecular structure (200,250). For example, given the three atomic sites I, K, and H (which are chosen to be non-colinear) in the molecular structure (200,250), the vectors i=I->H and j=I->K can be formed. Since, the three points are assumed to be non-colinear, the cross-product k=i x j of the two vectors i and j is well-defined and perpendicular to the plane defined by the vectors i and j. The unit vectors u1, u2 and u3 along the directions defined by the three vectors i, j, and k respectively define a skewed local coordinate frame 245. This coordinate frame 245 is called 'skewed' because in the general case the unit vectors i and j are not orthogonal to one another. However, it is possible that the formed skewed coordinate frames 245 consist of unit vectors u1 and u2 which are orthogonal.

Note that as described above, a local skewed coordinate frame 245 can be formed by selecting one (or both) of the atomic sites which define the rotatable bond 218, D or G (or D and G) and two (or one) of the remaining atomic sites of the given substructure (210,220). For example: a local skewed coordinate frame 245 for substructure 210 can be defined by using one of the atomic sites H, I, J, K, L, M, N, O, P and both D and G. Equivalently, a local skewed coordinate frame 245 for substructure 220 can be defined by using two of the atomic sites H, I, J, K, L, M, N, O, P and exactly one of D, G. In a similar manner, one or more local skewed coordinate frames 245 can be selected for substructure 210.

The global coordinate frame 235 is different from the skewed local coordinate frames 245 that one can form, because the skewed local coordinate frame's 245 position and orientation in the global coordinate frame 235 can vary as the respective molecule 200 undergoes rigid transformations (rotations 290 and translations 295). The same statement holds true when a rigid group (210,220) in the molecular structure (200,250) rotates 215 with respect to another rigid group (210,220) around the rotatable bond 218 which joins the two rigid groups 210 and 220.

Once a given skewed local coordinate frame 245 is formed by using sites from a molecular rigid substructure 220, the vector 238 that is associated with the rigid substructure can be represented in this frame. This representation can be either explicit or implicit.

In the explicit representation, the vector 238 has a fixed position and orientation in the selected skewed local coordinate frame 245. This position and orientation can be described, for example, in terms of a translation vector T connecting the center of the skewed local coordinate frame 245 to any fixed point SP along the axis (direction) 217 of the vector 238 (e.g. one of the end points D,G of the vector 238), and a rotation matrix R. The translation vector T gives the position of the point SP in the skewed local coordinate frame 245, whereas the rotation matrix R gives the orientation of the vector 238 in the same skewed local coordinate frame 245. Note that the rotation matrix can be equivalently described by listing the lengths of the projections of the vector 238 on the axes i, j and k of the skewed local coordinate frame 245. Alternatively, the rotation matrix can be described by listing the angles that the vector 238 forms with each of the axes i, j and k of the skewed local coordinate frame 245. In addition, other information, e.g. the identity of the rotatable bond 218—in the case that the vector 238 is defined in terms of such a rotatable bond, or, the magnitude of the vector 238 can be included in the representation; this additional information may be used for verification purposes. In this discussion, it has been assumed that all bonds of the molecular structure under consideration have been given unique labels.

The magnitude, position, and orientation of the vector 238 can be compactly represented in a matrix form by a slight modification of the 4×4 homogeneous transformation matrix that is very common in the computer graphics field. In particular, the modified transformation matrix can be built as the following diagram indicates by using the 3×3 rotation matrix R mentioned above, the 3×1 translation vector T, and the lengths of the 3 projections of the vector 238 on the axes i, j, and k of the skewed local coordinate frame 245:

$$\begin{bmatrix} ProjectionOnI & \\ ProjectionOnJ & R \\ ProjectionOnK & \\ T & 1 \end{bmatrix}$$

In the implicit representation, the position and orientation of the vector 238 in the selected skewed local coordinate frame 245 can be done by listing the identifying labels of the atomic sites D/G which help define the vector 238; the labels have to be listed in the order that defines the direction of the associated vector 238. In the implicit case, the position and orientation of the vector 238 in the skewed local coordinate frame 245 is generated from the labels of the defining atomic sites D, G and the description of the molecular structure 200 whenever such position and orientation information are needed. All other information, as explained in the explicit representation case can be obtained through on-line computation. Therefore, the implicit representation may decrease the storage requirements in the system 100.

Given the either implicit or explicit representation of vector 238 in a selected skewed local coordinate frame 245 suffices to determine the representation of vector 238 in the global coordinate frame 235.

As mentioned above, defining the coordinates (x, y, z) of three or more atoms (sites) (e.g. G–P) of a given rigid substructure 220 in the global coordinate frame 235 suffices to define a skewed local coordinate frame 245 as well as a global position and a global orientation for the rigid substructure 220 in the global coordinate frame 235. Consequently, defining the coordinates (x, y, z) of three or more atoms (sites) (e.g. G–P) of a given rigid substructure 220 in the global coordinate frame 235 suffices to define the position and orientation of the associated vector 238 in the global coordinate frame 235. This is achieved by making use of the either implicit or explicit representation of vector 238 in the skewed local coordinate frame 245 and applying a change of coordinate frames through known vector techniques to the global coordinate frame 235. Similarly, defining the coordinates (x, y, z) of three or more atoms (sites) (e.g. A–F) of a given rigid substructure 210 in the global coordinate frame 235 suffices to define the position and orientation of the associated vector 238 in the global coordinate frame 235. It is very important to note that if the vector 238 is defined in terms of the rotatable bond 218 that connects two rigid substructures 210 and 220, the position and orientation of the vector 238 in the global coordinate frame as determined by a skewed local coordinate frame 245 of a given substructure 210 will be identical to the position and orientation of the vector 238 in the global coordinate frame 235 as determined by a skewed local coordinate frame 245 of another given substructure 220; also note that in this particular case positioning and orienting the vector 238 in the global coordinate frame 235 constraints the position and orientation of the rigid substructures at its two ends, but does not fully specify it: indeed, each of the rigid substructure (210,220) still has one degree of freedom, namely the ability to rotate around the axis of the vector 238 with respect to the other substructure (220,210).

Figure 2B:
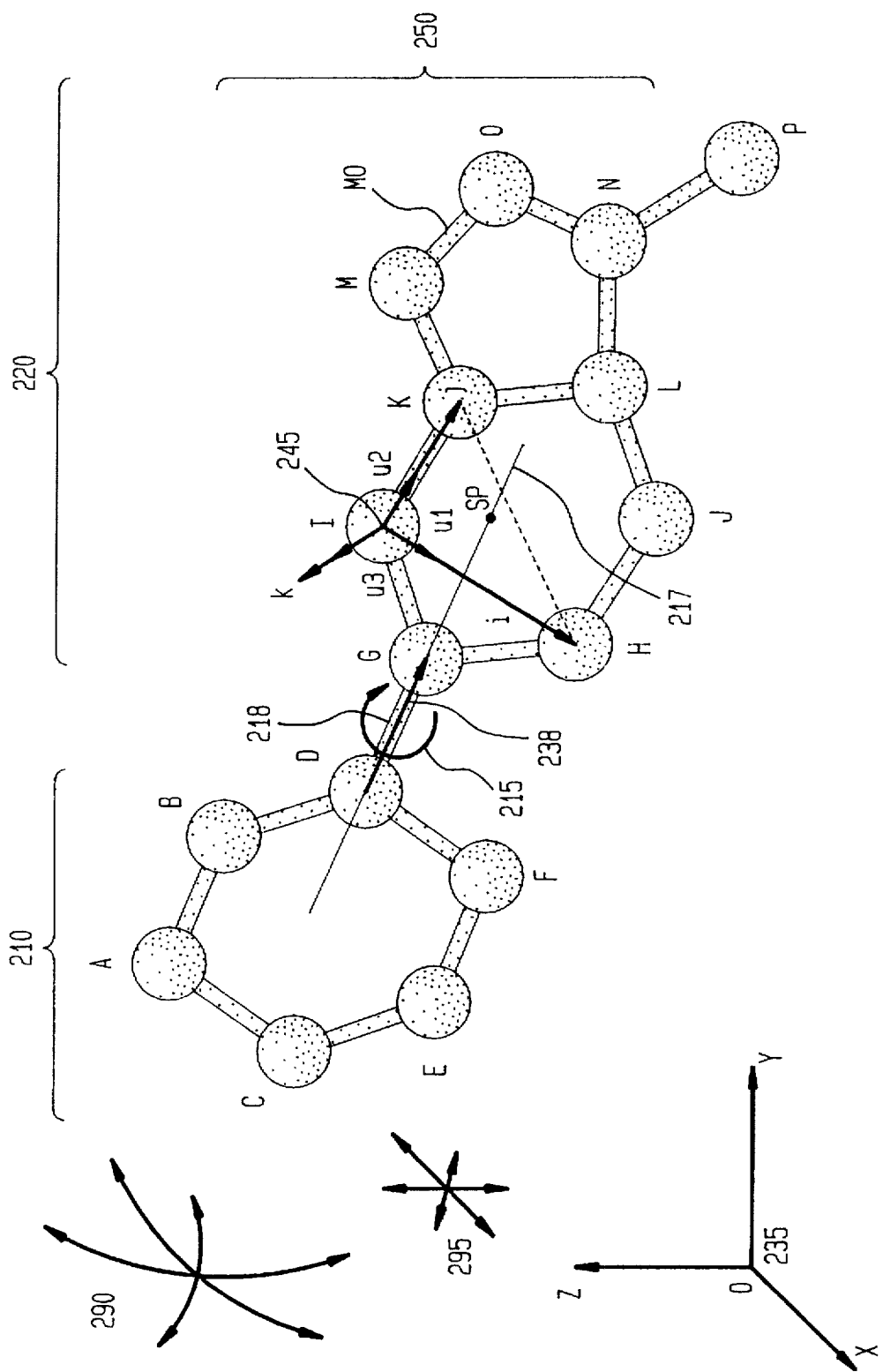

FIG. 2B is a diagram showing a second molecular conformation 250 of the molecular structure 200, the global coordinate frame 235, the skewed local coordinate frame 245, and the invariant vector 238 of FIG. 2A.

The term conformation is used to refer to any of a set of possible configurations in three-dimensional space that a given molecular structure (200,250) can assume due to an inherent structural flexibility; this flexibility is typically the consequence of rotatable and/or flexible bonds which exist in the molecule. The analysis herein concentrates on rotatable bonds only and assumes that the exhibited structural flexibility is the result of rotations of rigid substructures about such rotatable bonds. Typically, there is an infinity of such configurations with some of them being more energetically favorable than others. Also steric considerations may further limit the set of possible conformations.

As described above, in any conformation 250 of the molecular structure 200, the position and orientation of the rotatable bond 218 with respect to a skewed local coordinate frame 245 of a substructure (210,220) will remain the same (invariant). Similarly, the position and orientation of the rotatable bond 218 with respect to a skewed local coordinate frame 245 of a substructure (210,220) will remain the same (invariant) when the entire molecular structure 200 rotates and translates in the global coordinate frame 235. This is due to the fact that the skewed local coordinate frame 245 and the rotatable bond 218 are always in a fixed position and orientation with respect to one another, despite any rotation 215 of the rigid substructure 220 about the rotatable bond 218, and any translation 295 and/or rotation 290 of the entire molecular structure 200 or any of its conformations 250.

In order to create a set of descriptive indices for the molecular structure (200,250), tuples of atomic sites (and/or 'dummy' sites, described below) have to be selected. These tuples can be used to form skewed local coordinate frames 245. The tuples have tuple attributes that can include among other things geometric features, order, and vector relationships defined by the atomic sites comprising the tuple (see the description of FIG. 3).

In addition, one or more sets of atomic sites (and/or 'dummy' sites), for example the ring K–P, can be identified in the molecular structure (200,250) as having 'characteristics.' These characteristics are particular to the set of atomic sites K–P and can include: chemical (e.g. valence, atomic weight, atomic type etc.) and/or physical (e.g. electrostatic, hydropathy, etc.) properties of the set of atomic sites, other attributes, etc. In what follows, these sets of atomic sites K–P are referred to as 'site sets.'

Therefore, if one or more of the atomic sites participating in a tuple is also a member of one or more of the site sets, the characteristics of the site sets of which the atomic site in the selected tuple is a member, can also be associated with the tuple. Thus, these characteristics can be used to augment the index derived from the tuple and make it more descriptive.

The position and orientation of the vector 238 is represented in each of the skewed local coordinate frames 245. The representation of the vector 238, invariant in each of the skewed local coordinate frames 245, is associated via a data structure (see descriptions of FIGS. 4 and 5 below) to the index that is derived from the tuple.

FIG. 3 is a sequence of drawings showing how site sets K–O are defined (FIG. 3A), dummy sites Du are defined and then used (FIG. 3B), and how tuples (typically 335,345,355) are defined by selecting a set of one or more atomic sites and/or dummy sites, Du, from the molecular structure 200. Each tuple (335,345,355) is used to define a specific skewed local coordinate frame 245.

A site set is a set comprising one or more atomic sites and/or one or more dummy sites of the molecular structure 200. One example of a site set could be a commonly occurring structure (e.g. a phenyl ring, or the ring K–O) in a database, D, of molecular structures 200. It is sometimes useful to replace such a structure with a single dummy site Du. An alternative way of defining a site set is to select atoms that share a common set of characteristics and/or attributes. For example, one could form a site set by collecting all the atomic sites that participate in an aromatic ring. Another site set could be formed by collecting all those sites that act as hydrogen donors (respectively acceptors). These site sets can also be replaced by a dummy unit in which case the dummy unit will inherit all the characteristics of the site set that is being replaced. For example, in FIG. 3A, the site set K–O is bound to atomic site P. When the site set K–O is replaced by the dummy unit Du (FIG. 3B), it is the dummy unit that will now be bound to the atomic site P instead of the site set K–O. Additionally, if the site set K–O has characteristics (e.g. hydropathy, certain electrostatic behavior, etc.) the dummy unit Du will inherit these characteristics as well.

A tuple is a set of one or more atomic sites and/or one or more dummy sites. Tuples comprising only one atomic (or dummy) site are useful in describing translations 295 of a rigid structure. In such cases, determining information about the rotation 290 may incur additional computational burden. Furthermore, information for creating indices may be limited to the characteristics of the single atomic (or dummy) site in the tuple. Similarly, tuples comprising only two atomic (or dummy) sites are useful in describing translations 295 of a rigid structure and they also constrain the rotation 290 in two degrees of freedom but do not fully specify the rotation: determining information about the rotation 290 will incur additional computational burden. In this case, information for creating indices may be limited to the characteristics of the two atomic (or dummy) sites in the tuple.

In the preferred embodiment, tuples are defined using three or more atomic (and/or dummy) sites. In a more preferred embodiment at least three atomic (and/or dummy) sites of the tuple are non-colinear. The tuples are used to define a skewed local coordinate frame 245 (as described above) and an index. If the tuple comprises four atomic (and/or dummy) sites, any three of which are non-colinear, then the cross product ixj (described above) can be replaced by the vector connecting the origin of the skewed local coordinate frame 245 to the fourth site.

Note that four or more atomic (and/or dummy) sites can be used. In this case, any three non-colinear atomic (and/or dummy) sites can be selected to determine the skewed local coordinate frame 245, whereas the remaining atomic (and/or dummy) sites can be used to further constraint the hypotheses generated during the matching stage of the method. See description of FIG. 6 below.

Note that none, some, or all of these attributes and characteristics can be used to form a number (index) uniquely describing the formed triangles which correspond to the tuples.

The vector 238 is rigidly placed in the skewed local coordinate frame 245 as described above. The vector 238 is then represented (implicitly or explicitly as described above) in the skewed local coordinate frame 245 of the formed triangle.

Tuples are formed during the performance of two processes contained in this invention: a reference storage process (see FIG. 5), and a matching process (see FIG. 6). In the reference storage process, tuples are formed by selecting atomic (and/or dummy) sites from the molecular structure (200,250). During the reference storage process, the tuples are formed by selecting from a set of atomic (and/or dummy) sites called the 'reference tuple-selection set.' The reference tuple-selection set includes all the atomic sites in a rigid substructure (210,220), all the dummy sites associated with a rigid substructure (210,220), and the atomic (and/or dummy) sites that are endpoints of any rotatable bond 218 attached to the given rigid substructure (210,220) but not included in the substructure (210,220). The reference tuple-selection set includes these atomic (and/or dummy) sites because tuples comprising one or more of these sites remain invariant despite rotation 215 about any rotatable bond 218. This is because, as explained above, the position and orientation of the rotatable bond 218 with respect to the skewed local coordinate frame 245 that the tuple defines will remain the same (invariant) when the rigid substructure 220 rotates with respect to the rigid substructure 210. Note further, that the position and orientation of the rotatable bond 218 is invariant in the skewed local coordinate frame 245 that the tuple defines despite any rotation 290 and translation 295 of the molecular structure (200,250). In a preferred embodiment, the tuples may be chosen from a proper subset of the reference tuple-selection set just defined.

During the matching test process, the tuples are formed by selecting from a set of atomic (and/or dummy) sites called the 'matching tuple-selection set.' Unlike the reference-tuple-selection set, the matching tuple-selection set could include all of the atomic (and/or dummy) sites of the entire molecular structure (200,250). In an alternative preferred embodiment, subsets of all these sites can be used to form the matching tuple-selection set. In a preferred embodiment, the atomic sites in both the reference tuple-selection, and the matching tuple-selection set will not include atomic (and/or dummy) sites which are too far from one another (e.g. more than 10 Angstroms apart).

The invention creates a plurality of tuples in both the reference storage 500 and the matching test 600 processes. In a preferred embodiment, as many tuples as possible are created by using the reference tuple-selection set (or the matching tuple-selection set). In another preferred embodiment, all possible tuples implied by these tuple-selection sets are created. In another preferred embodiment, all possible tuples, excluding redundant permutations of the tuple's members, implied by these tuple-selection sets are created.

Figure 3A:
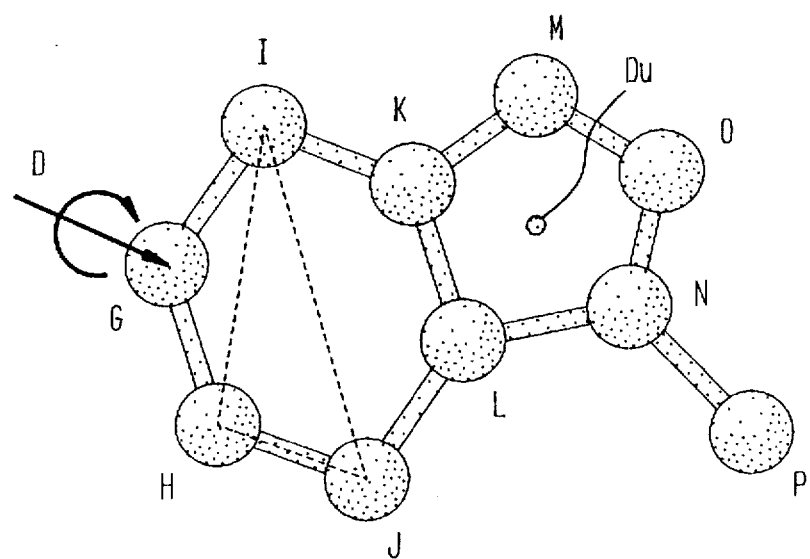
FIG. 3 is a sequence of drawings showing how site sets K–O are defined (FIG. 3A), dummy sites Du are defined and then used (FIG. 3B), and how tuples (FIGS. 3B–3E) are defined by selecting a set of one or more atomic sites and/or dummy sites Du from the molecular structure.
Figure 3B:
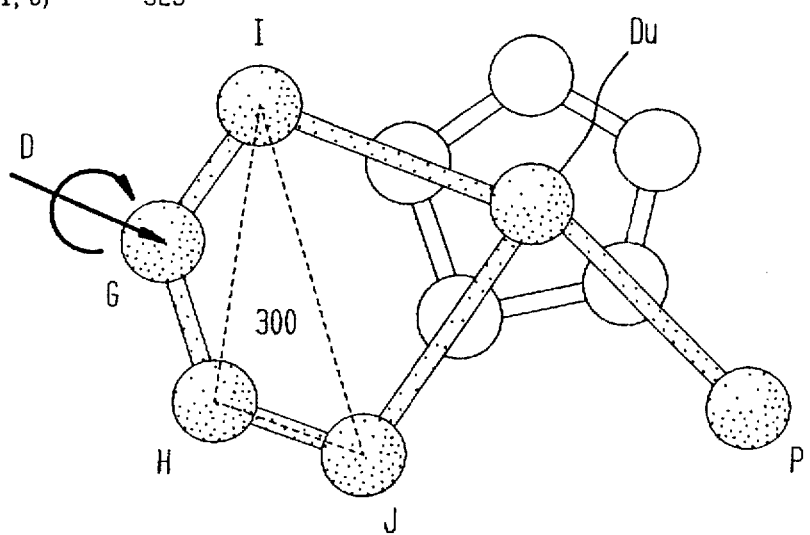
Figure 3C:
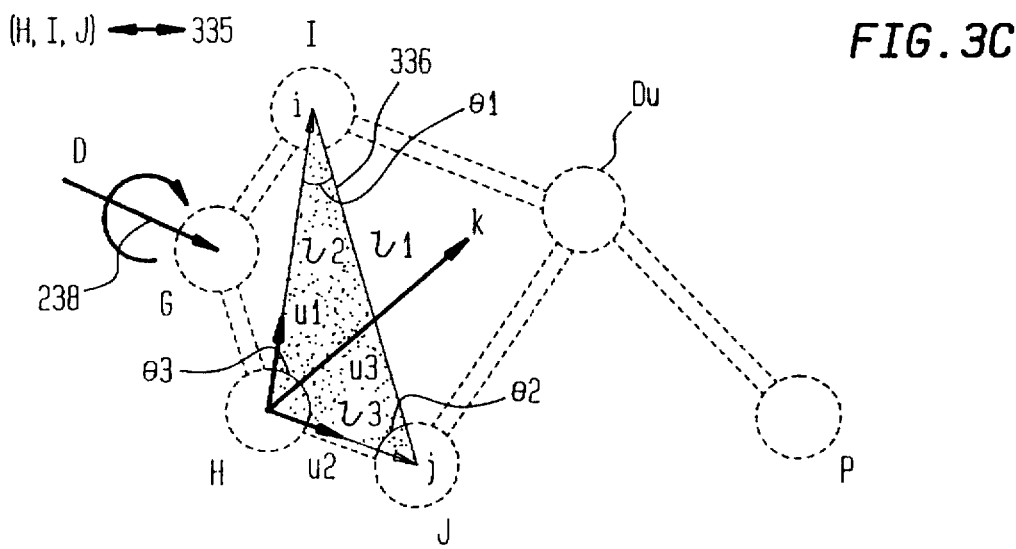
Figure 3D:
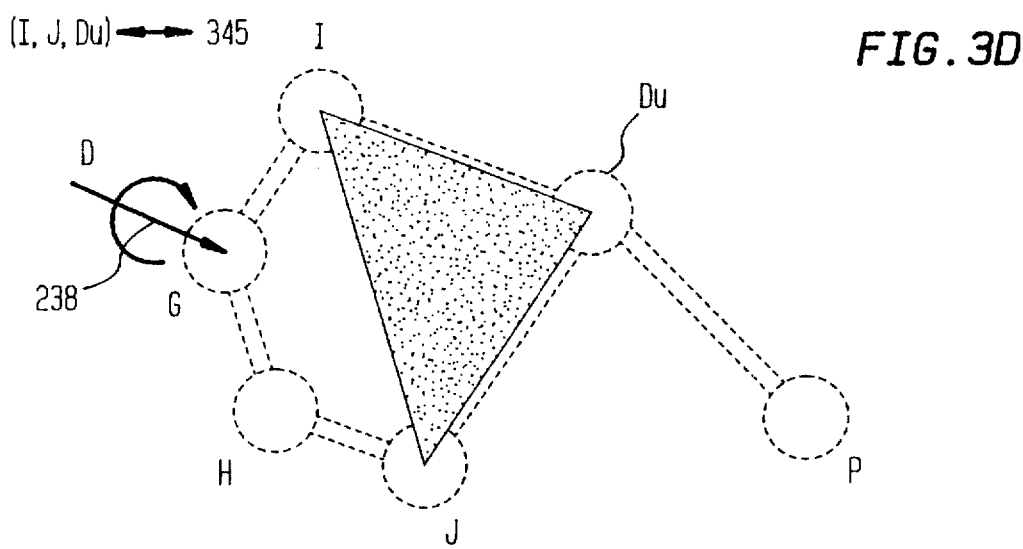

FIG. 3C is a representation of substructure 220 with attached rotatable bond 218 and the ring structure K–O represented by the dummmy site Du. A tuple 335 is formed by selecting three atomic sites H, I, J from the reference tuple-selection set including the set of atomic sites D, G, H, I, J, P and the dummy site Du. The tuple 335 defines a triangle 336 with attributes that include: geometric features (e.g. the lengths of the three sides of triangle 336, the angles of the triangle 336, the perimeter of the triangle 336 etc.), order information (which is implied by convention from the order in which the sites are selected), vector information, etc. For example, when the atomic sites are selected in the order H, I, J, the vector i (see discussion above) is defined as i=H->I, and the vector j (see discussion above) is defined as j=H->J; this convention is used consistently throughout the described process. Other conventions are possible. Alternatively, if the atomic sites are selected in the order I, H, J, the vector i (see discussion above) is defined as i=I->H, and the vector j (see discussion above) is defined as j=I->J. In both cases, the vector k is defined as k=ixj, as described above, and the vectors i, j, k define the skewed local coordinate frame 245 associated with the tuple 335.

When a given number, e.g. 3, of atomic sites are selected from the reference tuple-selection set, more than one tuple orderings are possible. In other words, the selected sites forming the tuple can be permuted to create other tuples. For example, the selected atomic sites H, I, J can form tuples 335 as follows: H-I-J, H-J-I, I-H-J, I-J-H, J-I-H, and J-H-I. In general, the number of ordered tuples that can be created by selecting k many sites from a reference tuple-selection set containing l many sites is given by $l!/(l-k)!$.

However, tuples 335 that are permutations of one another define the same geometric properties, e.g. the lengths of the sides of the triangle 336 etc. Therefore, in some preferred embodiments, redundant permutations of a given number of sites forming a tuple are not necessary. This is because all permutations of a given tuple 335 comprise the same set of atomic sites and therefore carry the same geometric features and vector information.

Order information can also be obtained if an ordering convention is imposed: all permutations of a given tuple 335 can be generated from a single normalized form of the tuple 335 by using the ordering convention. Therefore it suffices to consider only order-free combinations of atomic sites from the molecular structure (200,250); the number of possible (order-free) combinations that can be created by selecting k many sites from a reference tuple-selection set containing l many sites is given by $l!/(k!(l-k)!)$, which is smaller than the number of ordered tuples by a factor of $k!$. Accordingly, the storage requirements are reduced by the same factor at a minimal increase of the computational cost needed to carry out the necessary bookkeeping operations.

The process of selecting a single representative order-free tuple (=a combination) is called 'normalization.' Normalization involves determining a unique order when given a set of atomic sites; the imposed order is independent of the order in which the atomic sites are given. This is done by imposing an ordering convention to select a single representative 'normalized' tuple given a set of atomic sites. The atomic sites are ordered according to one preferred ordering convention by first determining the actual lengths of the sides of the shape formed by connecting the selected sites. Other ordering conventions are also possible. The first and second site in the order are those sites that are the furthest apart and form the longest possible side of a polygon that has each of the selected sites as a vertex. The third site in the order is the site that is the furthest apart from either of the first two sites and forms the next longest side of the polygon. The second site in the order then becomes the site at the vertex where the two previously formed sides intersect. The first site in the order the order then becomes the other site on the longest possible side. The ordering continues by choosing the fourth site as that remaining atomic site which is the furthest distance from the third site, the fifth site as the remaining atomic site which is the furthest from the fourth site and so on, until all the sites of the tuple 335 are ordered.

For example, using a tuple 335 of three atomic sites H, I, and J, a triangle 336 can be formed with its sides ordered according to the ordering convention described above. To do this, the longest distance I-J between any two of the sites H, I, J forms the longest side of the triangle 336. The second side is determined by the longest distance from either I or J to the remaining site H; in this case, this distance is I-H. Consequently, the second site in the order will be I because it is at the vertex shared by I-J and I-H; the first site in the order will be J which is the other vertex on the longest side; and, the third site in the order will be the only remaining site, H.

Note that enhancements to the convention are necessary in order to break any existing symmetries in the polygon. For example, if sides 1-H and I-J are equal in length, the ordering cannot be based on distance alone but other criteria should be used. These criteria could be based on other attributes of the tuple, such as atomic numbers of the atoms at the sites, chemical properties etc. For instance, in the case where 1-H and 1-J are equal in length, the atomic site I would be the second in the order because it is the vertex shared by the longest and second longest sides (equal sides). However, the order of atomic sites J and H is ambiguous and can be resolved for example by selecting that site from J and H with the highest atomic number as the first site in the order. Similar considerations could be used in the case where the triangle 336 is equilateral.

Once the tuple 335 is normalized, as described above, a unique index is formed that represents the tuple 335. This index can be created using any number of geometric features, attributes of the tuple's sites, chemical and/or physical information of the tuple or the tuple's atomic sites, etc. For example, assume that the atomic site J is a doubly-bonded nitrogen atom, I is a singly-bonded carbon atom, and atomic site H is a doubly-bonded carbon atom. Further note that the triangle 336 has a longest side of length 11, a second longest side of length 12 and a third site of length 13. Similarly, the triangle 336 has angles $\theta 1$, $\theta 2$, and $\theta 3$, respectively, corresponding to the ordered atomic sites J, I, and H. Given this information, a unique index describing this tuple J-1-H can be formed using zero or more of the sides 11–13, zero or more of the angles $\theta 1$–$\theta 3$, zero or more of the bond type designations (singly-bonded, doubly-bonded etc.), zero or more of the chemical types (nitrogen, carbon etc.), and/or zero or more of the physical attributes (atomic weight of the atoms at the sites, electronegativity, etc.), etc. In a preferred embodiment, the index is formed by using the lengths 11, 12, the angle $\theta 2$, and the atomic type of the atom at the second site in the order. In other embodiments, it may be desired to form indices if and only if the lengths 11 and/or 12 exceed a certain threshold, and/or the angle $\theta 2$ exceeds a certain threshold; typical thresholds may be 1 Angstrom for the length magnitude and 10 degrees for the angle magnitude. Finally, occasionally, it may be desirable to form the index by using the lengths 11, 12 and the largest angle in the triangle 336 formed by the tuple.

Figure 3E:
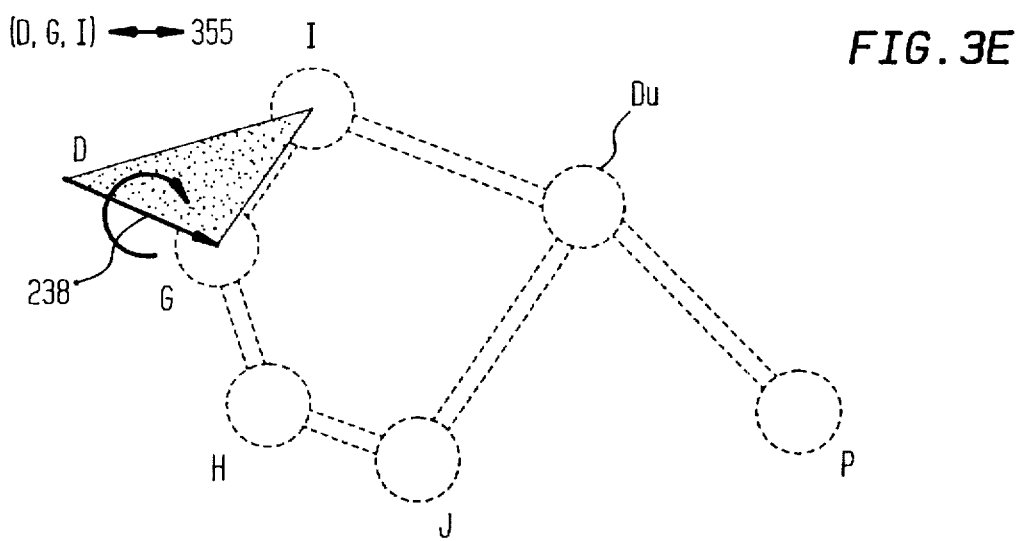

Given the discussion above, these tuples are created by making use of the reference tuple-selection set during the reference storage process 500, and of the matching tuple-selection set during the matching process 600. In a preferred embodiment, every possible combination of member-sites in either the reference tuple-selection set or the matching tuple-selection set is formed. In alternative embodiments, fewer tuples can be formed. For example, in FIG. 3D, a tuple 345 is formed by atomic sites I, J and the dummy site Du. This tuple is normalized as explained above and the corresponding unique index is created. In a similar manner, every other possible tuple, typically 355 (DGI), in FIG. 3E, is formed, normalized, and an index is created. Note that each of these indices is unique to the associated tuple and invariant with translation 295 and rotations 290 of the molecular structure (200,250), and any rotations 215 of either molecular substructure (210,220) about any rotatable bond 218.

In addition, for each tuple formed (335,345,355), a skewed local coordinate frame 245 associated with the tuple is derived in the manner described above. Vector information is associated with each vector 238 and is represented in each of the skewed local coordinate frames 245. Therefore, the vector information, the molecular structure 200 identity, the molecular substructure (210,220) identities, the rotatable bond 218 identity, the index 414, the tuple 335, and the skewed local coordinate frame 245 are all associated with one another.

Vector information is information about a given vector 238 and comprises the representation of the vector in the skewed local coordinate frame 245. In a preferred embodiment, this vector information is the explicit and/or implicit representation of the rotatable bond 218 as described above (FIG. 2A).

Note that a selected tuple 335 and the associated formed triangle 336 may also appear in a molecular structure other than 200. This necessitates the enhancement of the vector information with the inclusion of the identity of the molecular structure described above. This allows to identify the individual molecular structure 200 to which the vector information corresponds.

FIG. 4 is a block diagram of a data structure 400 that associates an index 414 corresponding to a tuple (typically 335,345,355) with information about the identities of the atomic sites participating in the tuple, and information that corresponds to the representation 238A of the vector 238 in the skewed local coordinate frame 245 of the tuple generating the index 414. Note that the tuple associated with index 414 may appear more than once in a molecular structure (200,250), or in more than one molecular structure (200, 250) in a database D containing a plurality of molecular structures (200,250). As a result, there is, in general, more than one entry 412 of vector information in a record 425 of the data structure 400. Consequently, each such entry, typically 412, of vector information includes identification information for each of the molecular structures 421A–421N in which the tuple creating the index 414 appears. A record 425 also contains the frame tuple field that comprises all the information pertaining to the index 410, the frame tuple that generated it and potentially other information.

As described above, the unique index 414 is formed that represents the tuple 335. This index 414 can be created using any number of geometric features, attributes of the tuple's sites, chemical and/or physical information of the tuple or the tuple's atomic sites etc. In addition, this index can be mapped to an offset in a one-dimensional linear array like 400 by using standard offset computation methods (e.g. 'stride' computation). For example, using 11, 12, θ2 and the SYBYL atomic type of the second in the (normalized) order atomic site to form an index, the computed offset (i.e., the location in the data structure 400) would be determined as follows:

1: quantize the value $V_{A_i}$ of each attribute $A_i$ (i=1, 2, 3, 4, . . . ) by taking the integer value of expression:

$$\frac{V_{A_i} - \min(A_i)}{\max(A_i) - \min(A_i)} \times (\text{STEPS}(A_i) - 1)$$

where min $(A_i)$ is the minimum value allowed for the attribute $A_i$, max $(A_i)$ is the maximum value allowed for the attribute $A_i$, STEPS $(A_i)$ is the data dependent number of quantization steps in which the interval $[\min(A_i), \max(A_i)]$ is divided (this number of steps is decided and made fixed prior to applying the method) and i runs through the set of attributes used to form the index 410. Example: if the length attribute 11 has value 1.3 Angstroms and assuming that the range of possible values, extending from 0.9 Angstroms to 4.5 Angstroms, has been divided into 64 quantization steps, the deduced quantized value for 11 would be:

$$\left[ \frac{1.3 - 0.9}{4.5 - 0.9} \times (64 - 1) \right] = 6.$$

In a similar manner, the quantized value of each attribute$A_i$ is determined. Note that for attributes$A_i$ that can inherently assume values from a finite set of integers (e.g. the 41 SYBYL atom types) the variable STEPS $(A_i)$ can be reduced to the cardinality of this set of integers.

2: Take the quantized values $A_i$, and compute the offset into linear array 400 using a 'stride' computation method. In this particular example, we have the following correspondences: $1_1 \leftrightarrow 11$, $A_2 \leftrightarrow 12$, $A_3 \leftrightarrow \theta_2$, $A_4 \leftrightarrow$ SYBYLAtomType. Computation of the offset gives:

$$\text{offset} = \begin{bmatrix} A_1 \cdot (\text{STEPS}(A_2) \cdot \text{STEPS}(A_3) \cdot \text{STEPS}(A_4)) \\ + A_2 \cdot (\text{STEPS}(A_3) \cdot \text{STEPS}(A_4)) \\ + A_3 \cdot \text{STEPS}(A_4) \\ + A_4 \end{bmatrix}$$

The structure 400 will be used by processes 500 and 600 as described below. The discussion so far implicitly assumed that each molecular structure (200,250) in the database D of molecules contains at least one rotatable bond 218.

But as it has been hinted on previously, this may not be true. Indeed, the following situations are possible: (a) rigid substructures with no rotatable bonds; in other words, some molecular structures in the database D may be rigid and contain no rotatable bonds; (b) rigid substructures with one rotatable bond emanating from the substructure; this is the case, for example, of the rigid substructures 210 and 220 in FIG. 2; and, (c) rigid substructures with more that one rotatable bonds emanating from the substructure. The fact that molecular structures with one or more of the above three characteristics are also present in the database D, necessitates a slight modification of the index generation procedure described above.

In the case of rigid molecular structures that contain no rotatable bonds (case (a) above), the vector 238 cannot be determined with the help of a rotatable bond. Instead, in a preferred embodiment, the vector 238 can easily be defined by identifying a pair of atomic sites: one such pair of sites, for example, could be formed by the pair of atomic sites that are the furthest apart in the molecular structure under consideration. Modifications of this procedure are also possible: the main objective here is the creation of a vector 238. The line connecting the two sites of the pair will correspond to the axis of vector 238. This can be seen as equivalent to having a 'fictitious rotatable' bond 218 that connects the rigid substructure 210 to itself. But, the direction of the vector 238 cannot be determined anymore by making use of the labels of the rigid substructures in question: a preferred embodiment introduces a modification according to which the direction of 238 is determined by making use of the numbers of the atomic sites that the (fictitious rotatable) bond connects: the convention for the direction is assumed to be from the lower-(higher-) numbered atomic site to the higher-(lower-) numbered atomic site consistently for all of one or more molecular structures 200 analyzed.

In the case of rigid molecular substructures with more than one rotatable bonds emanating from the substructure (case (c) above), there is a choice as to how the vector 238 is defined. For example, one of the rotatable bonds could be used in the definition of the vector 238. Alternatively, vector 238 could be defined with the help of a 'fictitious rotatable' bond.

When generating fictitious bonds, there may be situations where symmetries will need to be broken. For example: molecular structures that contain two pairs of atomic sites with the pairs' members at equal distance from one another. In order to resolve the issue, one embodiment could, for example, maintain the pair containing the lowest-numbered atomic site and discard the other.

With the described modification every molecular rigid substructure can now be equipped with 'a vector 238.' and which can be expressed as usual in each skewed local coordinate frame 245 that can be generated from the reference tuple-selection set.

Process 500 analyzes a set of one or more molecular structures (200,250) in a database, D, containing a plurality of molecular structures (200,250) by determining for a plurality of indices 410 zero or more molecular structures (200,250) and/or substructures (210,220) that contain tuples that are similar with respect to the attributesA$_i$ used to determine the index 410, for which each one of these molecular structures (200,250) and/or substructures (210, 220) will generate an entry 412:

(a) identifying (421A–421N) one of the molecular structures (200,250) associated with a given vector 238;

(b) identifying the frame tuple that generated the index 414;

(c) identifying (422A–422N) the molecular substructure (210,220) from which the tuple was drawn;

(d) identifying (423A–423N) the substructure (210,220) attached to the end of the rotatable bond 218 which is opposite from the end attached to the molecular substructure from (b) at the array location of structure 400 corresponding to index 414. In addition, process 500 will augment these entries 412 with vector information 238A about vector 238 in each of the skewed local coordinate frames 245 represented by each of the indices 414 in the entire database, D, of molecular structures. Additional information may also be included in these entries 412.

Once process 500 populates the data structure 400, the data structure 400 contains all of the structures (200,250) and/or substructures (210,220) in the entire database, D, classified according to the tuple attributes which are used to determine the index 414, along with invariant information about the vector 238 (this vector may correspond to real of fictitious bonds) existing in those structures (200,250), and possibly other information.

FIG. 5 is a flow chart showing the steps of populating the data structure of FIG. 4 to contain structural information and other information about one or more reference molecules. This process is called the reference storage process 500. The process 500 associates an index 414 corresponding to a tuple (typically 335,345,355) with vector information 420 that corresponds to the representation 238A for each vector 238 associated with a rigid substructure, in the skewed local coordinate frame 245 of the tuple generating the index 414 for every molecule in the database, D, of a plurality of known molecules.

Process 500, begins by selecting 505 a molecule with an identification from the database, D of known molecules. This identification can be any known way of labeling a molecule as described above, e.g. a scheme for numbering the molecules.

Step 510 determines the number of rigid substructures (210,220) in the selected molecule 505. If step 512 determines that there is only one rigid substructure, this means that the molecule in question is rigid and a fictitious rotatable bond is generated 513 as described earlier; then this rigid substructure is selected 520. If there is more than one substructure, a pair of rigid substructures connected by rotatable bond 218 in the chosen molecule 505 is selected 515. A typical rotatable bond 218 between the selected 515 rigid substructures is a vector 238 with a position and orientation in the global coordinate frame 235, as described above in FIG. 2A.

In step 520, one of the substructures of the selected pair 515 of rigid substructures (210,220), or the only rigid substructure of the molecule is selected. Subsequently, in step 525, a vector 238 is determined for the selected 520 rigid substructure, and a reference tuple-selection set is created.

In steps 530, 535, 540, 545, 550 and 555, a tuple, the associated skewed local coordinate frame 245, and an index (=reference frame tuple index) in the data structure 400—the index being unique to the tuple—are generated for every tuple that can be formed from the reference tuple-selection set. In a preferred embodiment, only normalized tuples are used (see above).

In step 530, a tuple is created by selecting among the members of the reference tuple-selection set. In step 535, a skewed local coordinate frame 245 is generated from the tuple created in 530, as described in FIGS. 2 and 3 above; the vector 238 that is associated with the selected 520 rigid substructure is represented 540 in the skewed local coordinate frame 245 defined by the tuple. Various ways of representing 540 the vector 238 are described above.

In step 545, the index 410 associated with the created tuple 530 is generated (see above for preferred embodiments for generating indices). In step 550, the representation 540 of the vector 238 is stored in the array/data structure 400 as an entry 412. Note that entry 412 is associated with the index 414 corresponding to the selected/created tuple 530. In step 555, the process 500 determines whether there are more tuples to be created 530 from the members of the reference tuple-selection set 525. If there are more tuples to be created, steps 530, 535, 540, 545, 550 and 555 are repeated. If there are no more tuples to be created 555, the identified molecule 505 is checked 560 to determine if both rigid substructures in the selected 520 pair of substructures 210,220 have been processed—by 'process' here is meant that an entry 412 is made in the data structure 400. If one of the substructures of the selected pair 515 still remains unprocessed 560, the unprocessed substructure is selected 520 and steps 525, 530, 535, 540, 545, 550 and 555 are repeated. If both substructures of the pair have been processed 560, the process 500 determines whether there are more pairs 565 of substructures 210,220 in the selected molecule 505 that are connected by rotatable bonds 218. If there are more pairs of substructures 565 connected by rotatable bonds in the molecule, the process is repeated starting at step 515.

When all of the pairs of substructures connected by a rotatable bond 218 in the selected molecule 505 have been processed, the process 500 determines 570 if there are any unprocessed molecules in the database D. If there are, process 500 begins again with step 505 with a newly selected molecule. If there are not, the process 500 terminates 575 having populated data structure 400 with all possible representations 412 of each vector 238, in all skewed local coordinate frames 245, of each molecule 505 in the database D. Note that, more than one representation of a vector 238 (e.g. 412A–412N) can be placed in the data structure 400 as associated with a given index 414 identifying a record 425 of the data structure 400.

FIG. 6 is a flow chart showing the steps of the matching process 600. The matching process uses the data structure 400 that was populated by the reference-storage process 500.

Process 600 forms tuples from the matching tuple-selection set of any given test molecule and a set of indices 410 corresponding to these tuples, in the manner described above. This set of indices is the 'test index' set. Given the information in the data structure 400, and the test-index set, process 600 can determine those structures (200,250) and/or substructures (210,220) of all the molecules in the database that contain tuples which share identical attributes $A_i$ with the tuples of the test molecule used to generate the test-index set. Further, process 600, using tallying data structure 700 and the information (410,420), can determine whether all or part of the test molecule is identical to one or more structures (200,250) and/or substructures (210,220) in the database.

Process 600 begins by selecting 605 a test molecule from a collection of one or more test molecules. This test molecule is checked against the database D, to identify those molecules of D containing molecular substructures (210, 220) that match the test molecule. By 'match' here it is meant that: (a) the identified molecule (or molecules) in D is identical to the test molecule; or, (b) the identified molecule (or molecules) in D contains substructures (210, 220) whose parts match the test molecule in its entirety; or, (c) the test molecule contains a part that matches the identified molecule (or molecules) in D in its entirety; or, (d) the test molecule contains a part that matches parts of one or more rigid substructures in the identified molecule (or molecules) of D. Notice that the test molecule and the identified molecule (or molecules) from D need not be in the same conformation. The process 600 in essence determines whether the test molecule matches one or more molecules in D, for a given conformation of the latter. However, it should be noted that the process 600 does not determine the required rotation and translation transformations that would put the identified molecule(s) in the conformation that will best register with the test molecule. Due to the fact that the knowledge of the position and orientation of the rotatable bond 218 in the global coordinate frame 235 constrains but does not fully specify the position and orientation of the rigid substructures attached at its endpoints, considerable computational expense is required to determine such conformations. This issue, called recognition, is addressed by U.S. patent application Ser. No. 08/577,353 and titled "System and Method for Conformationally-Flexible Recognition" to I. Rigoutsos filed on the same date as this application and which is herein incorporated in its entirety.

In the optional step 610, the process 600 determines if there is one or more rotatable bonds in the test molecule using any one of the standard approaches By doing this, the rigid substructures (210,220) in the test molecule are identified.

If there is only one rigid substructure, that rigid substructure is selected 620. If there is more than one substructure, two rigid substructures connected by rotatable bond 218 in the test molecule 605 are selected 615.

In step 620, one of the substructures of the selected pair 615 of rigid substructures (210,220) is selected. A matching tuple-selection set for the selected substructure of the test molecule is created 625.

In steps 630, 635, 645, a tuple, the associated skewed local coordinate frame 245, and an index (=test frame tuple index) unique to the tuple is generated for every tuple that can be formed from the matching tuple-selection set. In a preferred embodiment, only normalized tuples are used (see above).

In step 630, a tuple is created by selecting among the members of the matching tuple-selection set. In step 635, a skewed local coordinate frame 245 is generated from the tuple created in 630, as described in FIGS. 2 and 3 above. In step 645, the test frame tuple index 645i associated with the created tuple 630 is generated (see above for preferred embodiments for generating indices).

Note that steps 610, 615, 620, 625, 630, 635 and 645 are performed for the test molecule in an identical way as the respective steps 510, 515, 520, 525, 530, 535 and 545 are performed for all the reference molecules in the database D by process 500. Therefore, the test frame tuple index 645i is unique to the associated tuple and invariant under translation 295 and rotations 290 of the molecular structure (200,250) and any rotations 215 of any substructure (210,220) about rotatable bonds 218 present in the selected molecule 605.

In step 650, process 600 retrieves representations and other information from the data structure (array) 400 using the test frame tuple index. In the case where the test molecule is identical (in all the respects captured by the formed index: e.g. physical, chemical, geometrical etc.) to one or more of the molecules in the database D, there will be at least one entry 412 of vector information 420 in the record 425 accessed by each generated test frame tuple index 645i, in the data structure 400, that has the same vector information describing a vector 238 in the test molecule. The test frame tuple index 645i accesses the record 425 because the test frame tuple index 645i is identical to the reference frame tuple index 414 since they were both generated from the same molecular substructures (210,220) using the same steps (510, 515, 520,525,530, 535, 545 and 610, 615, 620, 625, 630, 635, 645 respectively).

However, note that there may be other molecules (or rigid substructures and/or parts of rigid substructures) in the database D that contain tuples generating reference frame tuple indices 414 that are the same as the test frame tuple indices 645i. This happens because the corresponding tuples are identical with respect to the chosen attributes 414 making up both the reference frame tuple index 414 and the test frame tuple index 645i. For example, in the case where the attributes are geometric (11/12/θ2, as above) and atomic type of one site (AtomicType as above), the tuple A-B-E in FIG. 2A will generate the same index irrespective of the actual chemical type of the atoms B and E, as long as the values of the attributes that form the index remain identical. Therefore, structure 400 has information that is useful in identifying one or more molecules from the database D that match (see above for a definition of 'match') a given test molecule by determining the frequency of occurrence of implicit or explicit information given by the vector information 420 in one or more of the entries 412A–412N, as described below.

After the vector information for the rotatable bonds is retrieved in step 650, the vector information 420 for each entry 412A–412N of the record 425 accessed by the test frame tuple index 645i, is used to recover the position and orientation, in the global coordinate frame 235, of each of the vectors 238 contained in each entry 412A–412N in the record 425. These recovered instances of vector 238 may also be referred to as test vectors in this discussion. The recovery is accomplished by using the representations of each vector 238 contained in entries 412A–412N and standard vector analysis methods; for each entry in each record with a reference frame tuple index matching the test frame tuple index, we produce a voting record in a voting data structure 655, the voting record containing placement information in the global coordinate frame 235, for each vector 238 whose representation is contained in entries 412A–412N. In alternative preferred embodiments, molecular identity 421A–421N, substructure (210,220) identity 422A–422N, and/or substructure (210,220) identity 423A–423N, can be used in addition to the recovered placement information when populating the voting table.

In step 660, each of the voting records produced in step 650 is entered in the voting table (see 700 below). Clearly, step 650 will produce many identical voting records, i.e. voting records that contain the same placement information, molecular identity information, and substructure identity information. This is the result of more than one frame tuples corroborating a certain placement in the global coordinate frame 235 for vector 238 associated with a given molecule's rigid substructure. The extent of matching between a part of a test molecule and one or more parts of one or more substructures of one or more molecules in the database D is directly related to the multiplicity of such identical voting records, or equivalently, to frequency of occurrence of each distinct voting records in the voting table 700.

Once all voting records produced using the items in the entries 412A–412N of the vector information 420 for the accessed record 425 are entered in the voting table then the process 600 determines 665 whether there are more tuples to be created 630 from the members of the reference tuple-selection set 625. If there are more tuples to be created 665, steps 630, 635, 645, 650 and 655 are repeated. If there are no more tuples to be created 665, the test molecule 605 is checked 670 to determine if both substructures in the selected 620 pair of substructures (210,220) have been processed. The unprocessed substructure is selected 620 and steps 625, 630, 635, 645, 650 and 655 are repeated. If both substructures of the pair have been processed, the process 600 determines whether there are more pairs of substructures 210,220 in the selected molecule 605 that are connected by rotatable bonds 218. If there are more pairs of substructures connected by rotatable bonds in the molecule, the process is repeated 672 starting in step 615.

Having completed the processing of the selected test molecule 605, the voting table 700, shown in FIG. 7, has been populated by voting records 725 produced by the entries of the data structure 400.

Each record 725 of the voting table has an address 710, and contains the reference molecule identity information, the reference rigid substructure identity information, and placement information for each vector 238 whose representations are contained in entries 412A–412N of record 425 accessed by the test frame tuple index 465i.

In a preferred embodiment, the molecule identity 736, and/or the rigid substructure 210 identity 738, and/or the rigid substructure 220 identity 740 are used to compute the address 710 of each voting record. The address 710 is determined by the 'stride'-computation method described above. In an alternative preferred embodiment, the placement information for each vector 238 whose representations are contained in entries 412A–412N of record 425 can be used to derive the address 710 of the record 725.

Returning now to FIG. 6, the populated voting table 700 is used to determine: (i) the identity of one or more molecules in the database D, (ii) the identity of one or more rigid substructure in each molecule, and (iii) the position and orientation of the vector 238 associated with each rigid substructure, so that (a) a rigid substructure in each such molecule is the best candidate for matching a substructure in the test molecule, and (b) when such a rigid substructure is placed in the global coordinate frame 235 so that the position and orientation of the associated vector 238 matches the one that has been determined in (iii), each identified molecule will be in best registration with the test molecule. Notice that there may be more than one molecules in the database D, that are best candidates for matching a substructure in the test molecule, and this is a consequence that a given test molecule substructure may be shared by more than one molecules in the database D. Determining these answers (i), (ii) and (iii) can be done by subselecting those records from the voting table 700 with a count (frequency) exceeding a predetermined threshold 675. These selected records 725 represent the reconstructed items with properties (a) and (b) above. For the purposes of the invention described herein, it suffices to report the identity of the molecule (or molecules) in the answers that exceeded the predetermined threshold.

Occasionally, it may be desirable to use those answers obtained from table 700 and which refer to the same molecule from database D in order to form that conformation of the molecule that is in agreement with as many of these answers as possible. If the molecule in question is put in this conformation it will be in its best possible registration with the test molecule, as a whole. The quality of the registration between the two molecules will vary as a function of the actual degree of similarity between them when all of the conformations of the identified molecule are taken into consideration. Unfortunately, the underconstraining nature of the answers obtained from the table 700 necessitates a considerable investment in computational power. This issue has already been addressed above in the paragraph that discusses the distinction between 'identification' and 'recognition.'

Given this disclosure one skilled in the art could develop equivalent alternative embodiments for molecular identification that are also within the contemplation of the inventors.

We claim:

1. A method for storing a representation of one or more reference molecules in a memory in a computer system, the method executed on a computer system and comprising the steps of:
   a. identifying either one or more rigid substructures of the reference molecule, each of the rigid substructures having one or more atomic sites, each of the atomic sites being connected to zero or more atomic sites in the rigid substructure with a non-rotatable bond, each rigid substructure having a global position and a global orientation in a global coordinate frame;
   b. defining a vector with a magnitude and direction with a fixed position and orientation with respect to the rigid substructure;
   c. selecting a set of three or more sites, the set of sites forming a frame tuple, at least one of the sites being non-colinear with the remaining sites, the sites being in a fixed position with respect to the rigid substructure, and the frame tuple defining a three-dimensional skewed local coordinate frame;

27 d. selecting one or more of the frame tuples and generating a frame tuple field with information associated with each of the selected frame tuples; and e. storing a record in a data structure, the data structure having a plurality of records, each record containing the frame tuple field and a vector field, the vector field containing vector information relating to the vector as well as information about the identities of the molecule and rigid substructure having the sites forming the frame tuple.

2. A method, as in claim 1, where the information in the frame tuple field is an index.

3. A method, as in claim 2, where the index is derived from physical information that is characteristic, of one or more of the sites of the frame tuple.

4. A method, as in claim 3, where the index is derived from chemical information that is characteristic of one or more of the sites of the frame tuple.

5. A method, as in claim 2, where the index is derived from geometric information relating to zero or more of the sites of the frame tuple, physical information that is characteristic of zero or more of the sites of the frame tuple, and chemical information that is characteristic of zero or more of the sites of the frame tuple.

6. A method, as in claim 3, where the index is derived from geometric information relating to the set of sites.

7. A method, as in claim 3, where the index is derived from one or more of the distances between any two sites in the set of sites.

8. A method, as in claim 3, where the index is derived from one or more of the angles in one or more of the triangles formed by any 3 sites in the set of sites.

9. A method, as in claim 3, where the index is derived from a combination of zero or more angles in one or more of the triangles formed by any three sites in the set of sites and zero or more distances between any two sites of the set of sites.

10. A method, as in claim 3, where the index is derived from areas formed by using at least three sites in the subset of sites.

11. A method, as in claim 3, where the index is derived from ratios of areas formed by using at least three sites in the subset of sites.

12. A method, as in claim 1, where the vector information further includes other information.

13. A method as in claim 12, where the other information includes any one or more of the following: molecular identity, substructure identity, atomic site information, and non-atomic site information, and information about the cardinality and identity of the vector.

14. A method as in claim 13, where the other information further includes any one or more of the following: physical properties, and chemical properties.

15. A method, as in claim 14, where one or more of the sites in the set of sites is an atomic site rigidly connected to the rigid substructure.

16. A method, as in claim 15, where one or more of the sites is a non-atomic site.

17. A method, as in claim 16, where one of the sites is a first site on a first rigid substructure and another site is a second site on a second rigid substructure, and the first and second rigid substructures are connected via a rotatable bond.

18. A method, as in claim 17, where the first and second sites can be any of the following: an atomic site and a non-atomic site.

19. A method, as in claim 18, where the first site is a first atomic site, the second site is a second atomic site, and the

28 vector has the position, magnitude and orientation of a rotatable bond connecting the first and second atomic sites.

20. A method, as in claim 19, comprising the further step of: f. repeating steps d and e for one or more of the unselected frame tuples.

21. A method, as in claim 20, where steps d and e are repeated for all of the unselected frame tuples.

22. A method, as in claim 20, comprising the further step of: g. repeating steps c–f for one or more of the unselected set of sites.

23. A method, as in claim 22, where steps c–f are repeated for all of the unselected sets of sites.

24. A method, as in claim 21, comprising the further step of: h. repeating steps b–g for the remaining rigid substructure in the case where a pair of substructures was selected.

25. A method, as in claim 24, where steps b–g are repeated for all of the unselected pairs of substructures that are connected with a rotatable bond.

26. A method, as in claim 24, comprising the further step of: i. repeating steps a–h for one or more unselected molecules.

27. A method, as in claim 26, where steps a–i are repeated for all unselected molecules.

28. A method, as in claim 19, where the vector information uniquely identifies the vector in the skewed local coordinate frame and the vector information remains invariant under any rotation and translation of the set of sites defining the skewed local coordinate frame.

29. A method, as in claim 28, where the vector information is information about an identity, a position, a vector magnitude and a vector orientation of each of the vectors represented in the local skewed coordinate frame.

30. A method, as in claim 29, where the vector information contains the projection of the vector on one or more axes of the local skewed coordinate frame.

31. A method as in claim 29 where two or more of the sites are atomic sites of the molecule including a first and second atomic site and the first and second atomic site define the position, magnitude and orientation of the vector.

32. A method as in claim 29, where the vector information includes a point position of a fixed point along the length of the vector, the vector magnitude, and the vector orientation.

33. A method as in claim 29, where the vector information includes the position being determined by two vector sites, the vector sites being sites in the set of sites, and the vector information further including the magnitude and the orientation of the vector.

34. A method as in claim 33, where one or more of the vector sites is an atomic site.

35. A method as in claim 34, where one or more of the vector sites is a non-atomic site.

36. A method as in claim 29, where the position, magnitude and orientation of the vector are represented by a matrix.

37. A method for storing a representation of one or more reference molecules in the memory of a computer system, the method executed on a computer system and comprising the steps of:

a. identifying one or more rigid substructures of the reference molecule, each of the rigid substructures having one or more atomic sites, each of the atomic sites being connected to zero or more atomic sites with a non-rotatable bond, and each rigid substructure having a global position and a global orientation in a global coordinate frame;

b. defining a vector with a vector magnitude and a vector direction, the vector being fixed in position and orientation with respect to the rigid substructure;

c. selecting a set of three or more sites, the sites being in a fixed position with respect to the rigid substructure and any set of sites being a frame tuple that defines a skewed local coordinate frame, the skewed local coordinate frame having two or more sides, with an angle between one or more pairs of the sides;

d. selecting one or more frame tuples and generating one or more indices from information about each of the selected frame tuples; and e. storing a record in a data structure stored in the memory, the data structure having a plurality of records, and each of the records containing vector information associated with one of the indices and accessible by using the index.

38. A method, as in claim 37, where the index is generated from information from two of the sides, being a first side and a second side, and a first angle being the angle between the first and second sides.

39. A method, as in claim 38, where either the first or the second side has a magnitude above a length threshold.

40. A method, as in claim 38, where the first side is the longest side in the triangle formed by the three members of the frame tuple, and the second side is the second longest side of the triangle formed by the three members of the frame tuple.

41. A method, as in claim 40, where the first angle has a magnitude above an angle threshold.

42. A method, as in claim 41, where the angle threshold is 10 degrees.

43. A method, as in claim 37, where the first angle is the largest angle in the triangle formed by the three members of the frame tuple.

44. A method, as in claim 37, where the index is generated from information that further includes the chemical characteristics of one or more of the atomic sites participating in the frame tuple.

45. A method for determining the identity of one or more reference molecules that are structurally similar to a test molecule, the method executed on a computer system and comprising the steps of:

a. identifying one or more rigid test substructures of the test molecule, each of the rigid test substructures having one or more atomic sites, each of the atomic sites being connected to zero or more atomic sites in the rigid test substructure with a non-rotatable bond, each rigid test substructure having a certain position and a certain orientation in a three-dimensional global reference frame;

b. selecting a set of three or more test sites, the set of test sites being a test frame tuple, at least one of the test sites being non-colinear with the remaining test sites, the test sites being in a fixed position with respect to the rigid test substructure, and each of the test frame tuples defining a three-dimensional skewed local test coordinate frame;

c. selecting one or more of the test frame tuples and generating a test frame tuple index from information associated with the selected test frame tuple;

d. using the test frame tuple index, accessing one or more records in a data structure stored in the memory, the data structure having a plurality of records, each of the records containing a reference frame tuple field and a reference vector information field, the reference frame tuple field having a reference frame tuple index generated from a reference frame tuple defined by three or more reference sites on a rigid reference substructure of one of the reference molecules, the reference vector field having one or more entries, each entry containing reference vector information about the reference vector having a magnitude and direction and a fixed position and a fixed orientation with respect to one or more rigid reference substructures, each entry further having reference frame tuple information about the reference frame tuple, reference molecule identity information, and reference frame rigid substructure information;

e. for each entry in each record with a reference frame tuple index matching the test frame tuple index, constructing a test vector for each reference vector in the skewed local test coordinate frame in order to place the test vector in the global coordinate frame;

f. for each entry in each record with a reference frame tuple index matching the test frame tuple index, producing a voting record in a voting data structure, the voting record containing the reference molecule identity information, the rigid reference substructure identity information, a test vector position field with a position value and test vector orientation field with an orientation value, the position value matching the test vector positions the orientation value matching the test vector orientation, the molecule identity information matching the reference molecule identity, and the rigid reference substructure information field matching the reference substructure identity.

46. A method as in claim 45, where the reference frame tuple index is generated from the reference frame tuple and the test frame tuple index is generated from the selected test frame tuple by the same method.

47. A method as in claim 45, comprising the further step of:

g. repeating steps c–f for one or more of the unselected test frame tuples.

48. A method, as in claim 45, where steps c–f are repeated for all of the unselected test frame tuples.

49. A method, as in claim 47, comprising the further step of:

h. repeating steps b–g for one or more of the unselected set of test sites.

50. A method, as in claim 49, where steps b–g are repeated for all of the unselected sets of sites.

51. A method, as in claim 49, comprising the further step of:

i. repeating steps a–g for one or more of the unselected rigid test substructures.

52. A method, as in claim 51, where steps a–g are repeated for all of the unselected test substructures.

53. A method as in claim 51, where a multiplicity of occurrence is determined for one or more identical voting records, for each of one or more sets of identical voting records.

54. A method, as in claim 53, where the sets of voting records having a multiplicity value below a threshold are eliminated.

55. A method, as in claim 53, where the voting table record having the highest multiplicity of occurrence contains the identity of the reference molecule matching the test molecule, and the identity of the rigid reference substructure matching one or more of the test molecule rigid substructures.

56. A computer system for storing a representation of one or more reference molecules in a memory in the computer system and for comparing one or more of the reference molecules to a test molecule, comprising:

a. a database stored in the memory, the database having a representation of one or more rigid substructures of each of the reference molecules, each of the rigid substructures having one or more atomic sites, each of the atomic sites being connected to zero or more atomic sites in the rigid substructure with a non-rotatable bond, each rigid substructure having a global position and a global orientation in a global coordinate frame;

b. a set of three or more sites, the set of sites being in a selected rigid substructure, the set of sites forming a frame tuple, at least one of the sites being non-colinear with the remaining sites, the sites being in a fixed position with respect to the selected rigid substructure, and the frame tuple defining a three-dimensional skewed local coordinate frame; and c. a data structure, having a plurality of records, each record containing a frame tuple field and a vector field, the vector field containing vector information relating to each of one or more vectors as well as information about the identities of one or more of the molecules and one or more of the rigid substructures, each of the vectors having a magnitude and a direction, and a fixed position and orientation with respect to the selected rigid substructure and the selected rigid substructure being one of the rigid substructures.

57. A computer system, as in claim 56, further having a voting data structure, the voting data structure having a plurality of voting records, each of the voting records containing information including a reference molecule identity, a reference frame rigid substructure identity, and a placement information for each of one or more test vectors in the global coordinate frame having a test frame tuple index that is the same as a reference frame tuple index associated with the frame tuple field and the vector field, the test frame tuple index generated for each of one or more selected test frame tuples of the text molecule and from information associated with the selected test frame tuple, each of the selected test frame tuples being formed from a set of three or more test sites of the test molecule, at least one of the test sites being non-colinear with the remaining test sites, the test sites being in a fixed position with respect to the rigid test substructure on the test molecule, and each of the test frame tuples defining a three-dimensional skewed local test coordinate frame.

58. A system, as in claim 57, where a multiplicity of occurrence is determined for one or more identical voting records, for each of one or more sets of identical voting records.

59. A system, as in claim 58, where the sets of voting records having a multiplicity value below a threshold are eliminated.

60. A computer system for storing a representation of one or more reference molecules in a memory in the computer system and for comparing one or more of the reference molecules to a test molecule, comprising:

a. a database means stored in the memory, the database means for representing one or more rigid substructure means of each of the reference molecules, each of the rigid substructure means having one or more atomic site means, each of the atomic site means being connected to zero or more atomic site means in the rigid substructure means with a non-rotatable bond, each rigid substructure means having a global position and a global orientation in a global coordinate frame;

b. a set of three or more site means, the set of sites being in a selected rigid substructure means, the set of site means forming a frame tuple means, at least one of the site means being non-colinear with the remaining site means, the site means being in a fixed position with respect to the selected rigid substructure means, and the frame tuple means defining a three-dimensional skewed local coordinate frame means; and c. a data structure means for storing, a plurality of record means, each record means containing a frame tuple field and a vector field, the vector field containing vector information relating to each of two or more rectors as well as information about the identities of one or more of the molecules and one or more of the rigid substructure means, each of the vectors having a magnitude and a direction with a fixed position and orientation with respect to the selected rigid substructure means and the selected rigid substructure means being one of the rigid substructure means.

* * * * *